(12) United States Patent
Coghlan et al.

(10) Patent No.: US 7,482,344 B2
(45) Date of Patent: Jan. 27, 2009

(54) TRICYCLIC STEROID HORMONE NUCLEAR RECEPTOR MODULATORS

(75) Inventors: Michael Joseph Coghlan, Fishers, IN (US); Prabhakar Kondaji Jadhav, Zionsville, IN (US); James Joseph Droste, Indianapolis, IN (US); Jonathan Edward Green, Avon, IN (US); Donald Paul Matthews, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 112 days.

(21) Appl. No.: 10/576,901

(22) PCT Filed: Dec. 15, 2004

(86) PCT No.: PCT/US2004/039767

§ 371 (c)(1),
(2), (4) Date: Apr. 20, 2006

(87) PCT Pub. No.: WO2004/052847

PCT Pub. Date: Jun. 24, 2004

(65) Prior Publication Data

US 2007/0088016 A1    Apr. 19, 2007

Related U.S. Application Data

(60) Provisional application No. 60/530,992, filed on Dec. 19, 2003.

(51) Int. Cl.
| | |
|---|---|
| A61K 31/423 | (2006.01) |
| A61K 31/431 | (2006.01) |
| A61K 31/496 | (2006.01) |
| A61K 31/4433 | (2006.01) |
| C07D 265/30 | (2006.01) |
| C07D 401/14 | (2006.01) |
| C07D 417/10 | (2006.01) |

(52) U.S. Cl. .............. 514/234.5; 514/254.06; 514/338; 514/367; 514/375; 514/437; 544/107; 544/366; 546/273.7; 548/159; 549/16

(58) Field of Classification Search .......... 514/366, 514/375, 437, 454; 548/159, 221, 300.4; 549/16, 224
See application file for complete search history.

(56) References Cited

U.S. PATENT DOCUMENTS

| | | | |
|---|---|---|---|
| 2,891,957 | A | 6/1959 | Allen et al. |
| 5,093,210 | A | 3/1992 | Ohta et al. |
| 5,378,701 | A | 1/1995 | Ohshima et al. |
| 5,478,840 | A | 12/1995 | Ohshima et al. |
| 5,607,955 | A | 3/1997 | Ohshima et al. |
| 6,289,190 | B1 | 9/2001 | Amamiya et al. |

FOREIGN PATENT DOCUMENTS

| | | |
|---|---|---|
| JP | 01161245 | 6/1989 |
| JP | 02032358 | 2/1990 |
| JP | 04046352 | 2/1992 |
| JP | 05281765 | 10/1993 |
| WO | WO 99/33786 | 7/1999 |
| WO | WO 00/05984 | 2/2000 |
| WO | WO 2004/052847 | 6/2004 |

OTHER PUBLICATIONS

King, Med. Chem.: Principle and Practice (1994), p. 206-208.*
Hirabe, et al., "Lithium Aluminum Hydride Reduction of 1-Aryl-3-halopropenes, 1-Aryl-3-halobutenes. and (9-Anthryl)arylmethyl Halides. Nucleophilic Substitution vs. Single Electron Transfer," J. Org. Chem, vol. 50, pp. 1797-1802 (1985).
Tewari, et al., "Synthesis of Some New Exocyclic Olefins via Phosphonium Ylides," Journal of Chemical and Engineering Data, vol. 22, No. 3, pp. 351-352 (1977).
Ogata, et al., "Reactions of (9-Anthryl)arylmethyl Chloride and Its Homologues with Nucleophiles under Solvolytic Conditions. Notable Effects of Reaction Conditions and substituents on the Reaction Sites," J. Am. Chem. Soc., vol. 103, pp. 1145-1153 (1981).
Takagi, et al., "Protonation and Alkylation of Ambident (9-Anthryl)arylmethyl Anions," J. Am. Chem. Soc., vol. 105, pp. 4676-4684 (1983).
Tewari, et al.. "Studies on Ylides: Exclusive Carbonyl Olefination with Semistabilized Arsonium Ylides," Journal of Organomet. Chem.. vol. 112, pp. 279-284 (1976).
Tewari, et al., "Studies on Betaine Decomposition of Arsonium Ylides," Anorg. Chem. Org. Chem. vol. 35, No. 1, pp. 95-98 (1980).
Mustafa, "Reactions in Sunlight of (a) Phenanthraquinone. Retenequinone, and Chrysonequinone with Ethylenes; (b) Retinequinone and Chrysenequinone with Aromatic Aldehydes: and (c) o-Formylbenzoic Acid with isopropyl Alcohol," J. Chem. Soc., pp. S83-S86 (1949).
Buu-Hoi, et al., "1-Bromo-1,2,2-Triarylethylenes of the Xanthese Serie," J. Org. Chem., vol. 16, pp. 1633-1638 (1951).

(Continued)

Primary Examiner—Taofiq A Solola
(74) Attorney, Agent, or Firm—Alexander Wilson

(57) ABSTRACT

The present invention provides a compound of Formula (I) or a pharmaceutically acceptable salt thereof; pharmaceutical compositions comprising an effective amount of a compound of Formula I in combination with a suitable carrier, diluent, or excipient; and methods for treating physiological disorders, particularly congestive heart disease, hypertension, rheumatoid arthritis or inflammation, comprising administering to a patient in thereof an effective amount of a compound of Formula (I).

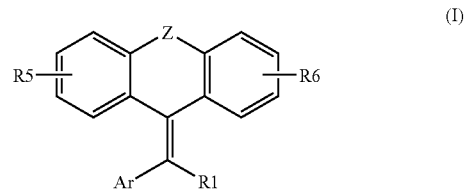

(I)

13 Claims, No Drawings

OTHER PUBLICATIONS

Bergmann. et al.. "Influence du methyle sur les specters des benzo- et dibenzofulvenes," Bull. Soc. Chim. Fr., pp. 669-680 (1951).

Bergmann, et al., "Fulvenes and Thermochromic Ethylenes. Part 57. The Wittig-Horner Reaction with Fulvene Ketones and Related Ketones," Synthesis, pp. 183-189 (1970).

Handoo, et al.. "Organic reactive intermediates: Part XII-Preparation and reactions of xanthenyland flavylium ylids," Indian Journal of Chemistry, vol. 29B, pp. 274-276 (1990).

Buu-Hoi, et al.. "1.2.2-Triarylethylenes Containing o- and m-Substituents," J. Org. Chem., vol. 22, pp. 1057-1059 (1957).

Decker. "Ueher die Beziehungen des doppelt gehundenen Kohlentoffs zum Stickstoff. Sauerstoff und Schwefel." Chem. Ber.. vol. 38, pp. 2493-2511 (1905).

Rabinovitz. et al.. "Fulvenes and Thermochromic Ethylenes. Part LXVIII. The Stereo-chemistry of the Wittig-Horner Reaction with Fulvenic and Related Ketones," J. Chem. Soc. Perkin Trans.2, pp. 1836-1838 (1972).

Ishikawa. et al.. "Wittig-Horner Reaction of Phosphonates Derived from Heteroniaanthracene Cations," Snythesis, pp. 608-609 (1978).

* cited by examiner

TRICYCLIC STEROID HORMONE NUCLEAR RECEPTOR MODULATORS

This is the national phase application, under 35 USC 371, for PCT/US2004/039767, filed 15 Dec. 2004, which claims the benefit, under 35 USC 119(e), of U.S. provisional application 60/530,992, filed 19 Dec. 2003.

BACKGROUND OF THE INVENTION

Nuclear hormone receptors are an evolutionarily conserved class of intracellular receptor proteins which have been termed "ligand dependent transcription factors". Evans et al., SCIENCE, 240: 889 (1988). The nuclear hormone receptor gene superfamily encodes structurally-related receptor proteins for glucocorticoids (e.g. cortisol, corticosterone, cortisone), androgens, mineralocorticoids (e.g. aldosterone), progestins, estrogen, and thyroid hormone. Also included within this superfamily of nuclear receptors are receptor proteins for vitamin D, retinoic acid, 9-cis retinoic acid, as well as those receptors for which no cognate ligands have been identified ("orphan receptors") Ribeiro et al., Annual Rev. Med., 46:443-453 (1995). Steroid hormone receptors represent a subset of the nuclear hormone receptor superfamily. So named according to the cognate ligand which complexes with the receptor in its native state, the steroid hormone nuclear receptors include the glucocorticoid receptor (GR), the androgen receptor (AR), the mineralocorticoid receptor (MR), the estrogen receptor (ER), and the progesterone receptor (PR). Tenbaum et al., Int. J. Biochem. Cell. Bio., 29(12):1325-1341(1997).

In contrast to membrane bound receptors, nuclear hormone receptors encounter their respective ligands following entry of the ligand into the cell. Once ligand binding occurs, the ligand-receptor complex modulates transcription of target genes within the cell nucleus. For example, most ligand-free nuclear receptors are bound in a complex with heat shock proteins (HSPs) in the cytoplasm. Following entry of circulating hormone into the cell, binding elicits a conformational change in the receptor, dissociating the receptor from the hsp. The ligand bound receptors translocate to the nucleus, where they as monomers as well as hetero- and homodimers in binding to particular hormone response elements (HREs) in the promoter regions of target genes. The HRE-receptor complex then, in turn, regulates transcription of proximally-located genes. (see Ribeiro et al., supra.). On the other hand, thyroid hormone receptors (TRs) and other non-steroid receptors such as vitamin D receptor (VDR) and retinoic acid receptors (RAR) are bound to their respective HRE in the absence of HSPs and/or cognate ligand. Hormones released from the circulation enter the cell, binding in the nucleus to these receptors which, in turn, hetero-dimerize to other nuclear receptors such as 9-cis retinoic acid (RXR). As with the steroid hormone nuclear receptors, following ligand binding, the ligand-bound receptor complex again regulates transcription of neighboring genes.

Mineralocorticoids and glucocorticoids exert profound influences on a multitude of physiological functions by virtue of their diverse roles in growth, development, and maintenance of homeostasis. The actions are mediated by the MR and GR which share approximately 94% homology in their respective DNA binding regions, and approximately 57% homology in their respective ligand-binding domains. Kino et al., J. of Endocrinology, 169, 437-445 (2001). In visceral tissues, such as the kidney and the gut, MR regulates sodium retention, potassium excretion, and water balance in response to aldosterone. In addition, MR expression in the brain appears to play a role in the control of neuronal excitability, in the negative feedback regulation of the hypothalamic-pituitary-adrenal axis, and in the cognitive aspects of behavioral performance. Castren et al., J. of Neuroendocrinology, 3, 461-466 (1993). GR, which is ubiquitously expressed in almost all tissues and organ systems, is crucial for the integrity of central nervous system function and the maintenance of cardiovascular, metabolic, and immune homeostasis. Kino et al., J. of Endocrinology, 169, 437-445 (2001).

Elevations in aldosterone levels, or excess stimulation of mineralocorticoid receptors, are linked to several physiological disorders or pathologic disease states including, Conn's Syndrome, primary and secondary hyperaldosteronism, increased sodium retention, increased magnesium and potassium excretion (diuresis), increased water retention, hypertension (isolated systolic and combined systolic/diastolic), arrhythminas, myocardial fibrosis, myocardial infarction, Bartter's Syndrome, and disorders associated with excess catecholamine levels. Hadley, M. E., ENDOCRINOLOGY, $2^{nd}$ Ed., pp. 366-381, (1988); and Brilla et al., Journal of Molecular and Cellular Cardiology, 25 (5), pp. 563-575 (1993). Additionally, elevated aldosterone levels have been increasingly implicated with congestive heart failure (CHF). In CHF, the failing heart triggers hormonal mechanisms in other organs in response to the attending reductions in blood flow and blood pressure seen with CHF. In particular, the kidney activates the renin-angiotensin-aldosterone system (RAAS) causing an increase in aldosterone production by the adrenals which, in turn, promotes water and sodium retention, potassium loss, and further edema. Although historically it was believed that aldosterone participated in the etiology of CHF only as a result of its salt retaining effects, several recent studies have implicated elevated aldosterone levels with events in extra-adrenal tissues and organs, such as myocardial and vascular fibrosis, direct vascular damage, and baroreceptor dysfunction. Pitt et al., New Eng. J. Med., 341:709-717 (1999). These findings are particularly significant since angiotensin converting enzyme (ACE) inhibitors, which were once thought to completely abolish aldosterone production, are now believed to only transiently suppress aldosterone production which has been shown to occur in extra-adrenal tissues including the heart and vasculature. Weber, New Eng. J. Med., 341:753-755 (1999); Fardella and Miller, Annu. Rev. Nutr., 16:443-470 (1996).

The involvement of aldosterone acting via MR in CHF was confirmed in the recently completed RALES (Randomized Aldactone Evaluation Study) study. Pitt et al., New Eng. J. Med., 341:709-717 (1999). The RALES study demonstrated that the use of Aldactone™ (spironolactone), a well-known competitive MR antagonist, in combination with standard CHF therapy, reduced cardiac related mortality by 30% and frequency of hospitalization by 35% in patients suffering from advanced CHF. However, spironolactone therapy has also been associated with attending side effects such as gastric bleeding, diarrhea, azotemia, hyperchloremic metabolic acidosis an type-4 renal tubule acidosis, nausea, gynecomastia, erectile dysfunction, hyperkalemia, and irregular menses. Thus, the mineralocorticoid receptor represents a viable target for CHF therapy either alone or in combination with conventional CHF therapies such as vasodilators (ACE inhibitors), inotropics (digoxin), diuretics, or beta blockers. Molecules, preferably non-steroids, which bind to the mineralocorticoid receptor and modulate receptor activity without the attending side effects of current therapies would be particularly desirable.

Finally, published international PCT application WO 02/17895 discloses that aldosterone antagonists are useful in the treatment of subjects suffering from one or more cognitive dysfunctions including, but not limited to psychoses, cognitive disorders (such as memory disturbances), mood disorders (such as depression and bipolar disorder), anxiety disorders, and personality disorders.

Glucocorticoids (e.g. cortisol, corticosterone, and cortisone), and the glucocorticoid receptor, have also been implicated in the etiology of a variety of physiological disorders or pathologic disease states. For example, cortisol hyposecretion is implicated in the pathogenesis of Addison's Disease and may result in muscle weakness, increased melanin pigmentation of the skin, weight-loss, hypotension, and hypoglycemia. On the other hand, excessive or prolonged secretion of glucocorticoids has been correlated to Cushing's Syndrome and may also result in obesity, hypertension, glucose intolerance, hyperglycemia, diabetes mellitus, osteoporosis, polyuria, and polydipsia. Hadley, M. E., ENDOCRINOLOGY, $2^{nd}$ Ed., pp. 366-381, (1988). Further, U.S. Pat. No. 6,166,013, issued Dec. 26, 2000, discloses that GR selective agents could modulate GR activity and, thus, be useful in the treatment of inflammation, tissue rejection, autoimmunity, malignancies such as leukemias and lymphomas, Cushing's syndrome, acute adrenal insufficiency, congenital adrenal hyperplasia, rheumatic fever, polyarteritis nodosa, granulomatous polyarteritis, inhibition of myeloid cell lines, immune proliferation/apoptosis, HPA axis suppression and regulation, hypercortisolemia, modulation of the Th1/Th2 cytokine balance, chronic kidney disease, stroke and spinal cord injury, hypercalcemia, hyperglycemia, acute adrenal insufficiency, chronic primary adrenal insufficiency, secondary adrenal insufficiency, congenital adrenal hyperplasia, cerebral edema, thrombocytopenia, and Little's syndrome. U.S. Pat. No. 6,166,013 also discloses that GR modulators are especially useful in disease states involving systemic inflammation such as inflammatory bowel disease, systemic lupus erythematosus, polyartitis nodosa, Wegener's granulomatosis, giant cell arthritis, rheumatoid arthritis, osteoarthritis, hay fever, allergic rhinitis, urticaria, angioneurotic edema, chronic obstructive pulmonary disease, asthma, tendonitis, bursitis, Crohn's disease, ulcerative colitis, autoimmune chronic active hepatitis, organ transplantation, hepatitis, and cirrhosis; and that GR modulating compounds have been used as immunostimulants, repressors, and as wound healing and tissue repair agents.

In addition, U.S. Pat. No. 6,166,013 also discloses that GR modulators have also found use in a variety of topical diseases such as inflammatory scalp alopecia, panniculitis, psoriasis, discoid lupus erythematosus, inflamed cysts, atopic dermatitis, pyoderma gangrenosum, pemphigus vulgaris, bullous pemphigoid, systemic lupus erythematosus, dermatomyositis, eosinophilic fasciitis, relapsing polychondritis, inflammatory vasculitis, sarcoidosis, Sweet's disease, type 1 reactive leprosy, capillary hemangiomas, contact dermatitis, atopic dermatitis, lichen planus, exfoliative dermatitis, erythema nodosum, acne, hirsutism, toxic epidermal necrolysis, erythema multiform, and cutaneous T-cell lymphoma.

Thus, it is clear that a ligand which has affinity for steroid hormone nuclear receptors, and particularly for MR and/or GR, could be used to modulate (i.e. repress, antagonize, agonize, partially antagonize, partially agonize) receptor activity and target gene expression, thereby influencing a multitude of physiological functions related to alterations in steroid hormone levels and/or steroid hormone receptor activity. In this regard, such ligands could be useful to treat a wide range of physiological disorders susceptible to steroid hormone nuclear receptor modulation.

Several art references disclose tricyclic-derivative molecules useful as, inter alia, photographic coupling and developing agents, thromboxane A2 modulators, and as histamine H2 antagonists. Further, tricyclic-derivative compounds have also been disclosed as having pharmacological utility as, inter alia, antidepressants and anti-inflammatory agents. Surprisingly, however, and in accordance with the present invention, applicants have discovered a series of tricyclic compounds, particularly thioxanthene derivatives, with affinity for the mineralocorticoid and/or glucocorticoid receptors. Such compounds could modulate MR or GR activity and, thus, have utility in the treatment of disorders related to alterations in mineralocorticoid or glucocorticoid hormone level and/or to alterations in MR or GR activity. As a further embodiment, the present invention also provides a novel series of novel non-steroidal tricyclic compounds that exhibit MR or GR affinity and modulating activity. Such methods and compounds could address a long felt and continuing need for safe and effective pharmaceutical interventions without the attending side effects of steroidal-type agents. The treatment of hormone related disorders is hereby furthered.

The following references describe examples of the state of the art as it relates to the present invention.

U.S. Pat. No. 5,024,912 discloses 5H Dibenzo (A,D) cycloheptenylidene and 5H Dibenzo (A,D) cycloheptanylidene derivatives as electrophotographic photosensitive agents.

U.S. Pat. Nos. 4,741,976, 4,539,507, 5,093,210, and 5,166,022 disclose the use of tricyclic molecules in electroluminescent devices.

U.S. Pat. No. 4,282,233 discloses tricyclic molecules (i.e. Loratadine (Claritin™) as H2 antagonists.

U.S. Pat. No. 4,999,363 (and family members) discloses tricyclic molecules as thromboxane A2 antagonists.

U.S. Pat. Nos. 5,378,701 and 5,478,840 and 5,607,955 disclose tricyclic molecules as angiotensin II antagonists.

U.S. Pat. No. 6,362,188 B1 discloses tricyclic molecules as farnesyl protein transferase inhibitors.

Published International PCT Application WO 99/33786 discloses tricyclic propanamide derivative molecules as anti-inflammatory agents. Published International PCT Application WO 96/19458 and U.S. Pat. Nos. 5,696,130; 5,994,544; 6,017,924, and 6,121,450 disclose quinoline derivative analogs as steroid hormone receptor modulators.

Co-pending International PCT Application PCT/US03/16213 discloses a genus of tricyclic derivative compounds functional as nuclear hormone receptor modulators, particularly MR and GR modulators.

Published International PCT Application WO 00/05984 discloses tricyclic derivatives as antiparasitic agents.

U.S. Pat. No. 2,891,957 discloses amino alkoxy phenyl methanes as estrogen antagonists.

The following literature references also provide examples of the state of the art:

Hirabe, Tomoatsu; Takagi, Masato; Muraoka, Kiyoshige; Nojima, Masatomo; Kusabayashi, Shigekazu; *J. Org. Chem.*; 50; 11; 1985; 1797-1802.

Tewari et al.; *J. Chem. Eng. Data*; 22; 1977; 351.

Ogata, Fujimaro; Takagi, Masato; Nojima, Masatomo; Kusabayashi, Shigekazu; *J. Amer. Chem. Soc.*; 103; 5; 1981; 1145-1153.

Takagi, Masato; Nojima, Masamoto; Kusabayashi, Shigekazu; *J. Amer. Chem. Soc.*; 105; 14; 1983; 4676-4684.

Tewari; Gupta; *J. Organomet. Chem.*; 112; 1976; 279,282, 283.

Tewari, R. S.; Suri, S. K.; Gupta, K. C.; Z. Naturforsch. B *Anorg. Chem. Org. Chem.*; 35; 1; 1980; 95-98.

Mustafa; *J. Chem. Soc.*; 1949; Spl. 83, 86.
Buu-Hoi; Xuong; *J. Org. Chem.*; 16; 1951; 1633, 1636.
Bergmann et al.; *Bull. Soc. Chim. Fr.* 1951; 669, 680.
Bergmann, E. D.; Solomonovici, A.; *Synthesis;* 1970; 183-189.
Handoo, Kishan L.; Kaul, Anju; *Indian J. Chem. Sect. B;* 29; 3; 1990; 274-276.
Buu-Hoi et al.; *J. Org. Chem.;* 22; 1957; 1057.
Decker; *Chem. Ber.;* 38; 1905; 2506.
Rabinovitz et al.; *J. Chem. Soc. Perkin Trans.* 2; 1972; 1836.
Ishikawa et al.; *Synthesis;* 1978; 608.

SUMMARY OF THE INVENTION

The present invention is directed to the discovery that certain tricyclic molecules, as defined below, are modulators of steroid hormone nuclear receptors and, therefore, may have utility as pharmaceutical agents. Accordingly, the present invention provides a compound of the formula:

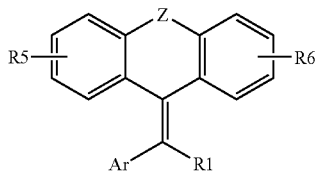

Formula I wherein,

Z represents $CH_2$, S, or O;

Ar represents a group of the formula:

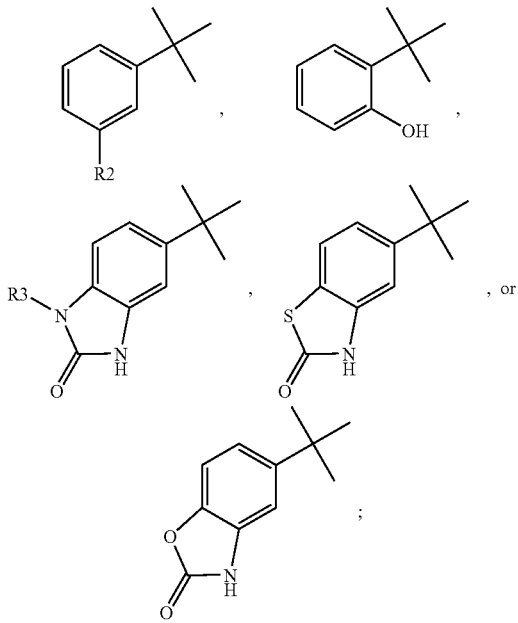

$R^1$ represents hydrogen or $(C_1-C_6)$alkyl;

$R^2$ represents hydroxy, amino, $(C_1-C_6)$alkoxy, $NHSO_2R^4$, provided that where $R^2$ represents hydroxy then Z is other than S $R^3$ represents hydrogen, $(C_1-C_6)$alkyl, heterocycle, substituted heterocycle, $(C_1-C_4)$alkyl-heterocycle, or $(C_1-C_4)$alkyl-substituted heterocycle, provided that where Ar represents:

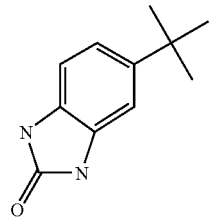

then Z is other than O;

$R^4$ represents independently at each occurrence $(C_1-C_6)$alkyl;

$R^5$ and $R^6$ represent independently at each occurrence hydrogen, halo, amino, cyano, hydroxy, $(C_1-C_6)$alkyl, halo$(C_1-C_6)$alkyl, $(C_3-C_7)$cycloalkyl, $(C_1-C_6)$alkoxy, $(C_1-C_4)$alkyl-$(C_3-C_7)$cycloalkyl, $(C_1-C_4)$alkoxy-$(C_3-C_7)$cycloalkyl, $NHR^7$, $N(R^7)_2$, $NHSO2R^7$, $SR^7$, $SO_2R^7$; and $R^7$ represents independently at each occurrence $(C_1-C_6)$alkyl, $(C_3-C_7)$cycloalkyl, phenyl, or heterocycle;

or a pharmaceutically acceptable salt thereof.

As another aspect, the present invention provides a method of treating a physiological disorder susceptible to steroid hormone nuclear receptor modulation comprising administering to a patient in need thereof an effective amount of a compound of Formula I as described herein and above. Examples of such disorders include Conn's Syndrome, primary and secondary hyperaldosteronism, increased sodium retention, increased magnesium and potassium excretion (diuresis), increased water retention, hypertension (isolated systolic and combined systolic/diastolic), arrhythmias, myocardial fibrosis, myocardial infarction, Bartter's Syndrome, disorders associated with excess catecholamine levels, diastolic and systolic congestive heart failure (CHF), peripheral vascular disease, diabetic nephropathy, cirrhosis with edema and ascites, esophageal varicies, Addison's Disease, muscle weakness, increased melanin pigmentation of the skin, weight loss, hypotension, hypoglycemia, Cushing's Syndrome, obesity, hypertension, glucose intolerance, hyperglycemia, diabetes mellitus, osteoporosis, polyuria, polydipsia, inflammation, autoimmune disorders, tissue rejection associated with organ transplant, malignancies such as leukemias and lymphomas, acute adrenal insufficiency, congenital adrenal hyperplasia, rheumatic fever, polyarteritis nodosa, granulomatous polyarteritis, inhibition of myeloid cell lines, immune proliferation/apoptosis, HPA axis suppression and regulation, hypercortisolemia, modulation of the Th1/Th2 cytokine balance, chronic kidney disease, stroke and spinal cord injury, hypercalcemia, hyperglycemia, acute adrenal insufficiency, chronic primary adrenal insufficiency, secondary adrenal insufficiency, congenital adrenal hyperplasia, cerebral edema, thrombocytopenia, and Little's syndrome, systemic inflammation, inflammatory bowel disease, systemic lupus erythematosus, discoid lupus erythematosus, polyartitis nodosa, Wegener's granulomatosis, giant cell arthritis, rheumatoid arthritis, osteoarthritis, hay fever, allergic rhinitis, contact dermatitis, atopic dermatitis, exfoliative dermatitis, urticaria, angioneurotic edema, chronic obstructive pulmonary disease, asthma, tendonitis, bursitis, Crohn's disease, ulcerative colitis, autoimmune chronic active hepatitis, hepatitis, cirrhosis, inflammatory scalp alopecia, panniculitis, psoriasis, inflamed cysts, pyoderma gangrenosum, pemphigus vulgaris, bullous pemphigoid, dermatomyositis, eosinophilic fasciitis, relapsing polychondritis, inflammatory vasculitis, sarcoidosis, Sweet's disease, type 1 reactive leprosy, capillary hemangiomas, lichen planus, erythema nodosum, acne, hirsutism, toxic epidermal necrolysis, erythema multiform, cutaneous T-cell lymphoma, psychoses, cognitive disorders (such as memory disturbances), mood disorders (such as depression and bipolar disorder), anxiety disorders, and personality disorders.

As a further aspect, the present invention provides a method of treating a physiological disorder susceptible to mineralocorticoid or glucocorticoid receptor modulation comprising administering to a patient in need thereof an effective amount of a compound of Formula I as described herein and above. As a more particular aspect, the present invention provides a method of treating a physiological disorder susceptible to mineralocorticoid or glucocorticoid receptor antagonism comprising administering to a patient in need thereof an effective amount of a compound of Formula I. As an even more particular aspect the present invention provides a method of treating hypertension (isolated systolic and combined systolic/diastolic), systolic and/or diastolic congestive heart failure, rheumatoid arthritis or inflammation comprising administering to a patient in need thereof an effective amount of a compound of Formula I as described herein and above.

As a separate aspect, the present invention also provides a method of modulating a steroid hormone nuclear receptor comprising contacting said receptor with an effective amount of a compound of Formula I. More particularly, the present invention provides a method of modulating the mineralocorticoid or glucocorticoid receptor comprising contacting said receptor with an effective amount of a compound of Formula I. More particularly still, the present invention provides a method of antagonizing the mineralocorticoid or glucocorticoid receptor comprising contacting said receptor with an effective amount of a compound of Formula I, as described herein and above.

In addition, the present invention provides pharmaceutical compositions of compounds of Formula I, including any pharmaceutically acceptable salts and hydrates thereof, comprising a compound, of Formula I in combination with a pharmaceutically acceptable carrier, diluent or excipient. This invention also encompasses novel. intermediates, and processes for the synthesis of the compounds of Formula I.

The present invention also provides the use of a compound of Formula I, or a pharmaceutically acceptable salt thereof, for the manufacture of a medicament for treating a physiological disorder susceptible to steroid hormone nuclear receptor modulation.

More particularly, the present invention provides the use of a compound of Formula I, or a pharmaceutically acceptable salt thereof, for the manufacture of a medicament for treating hypertension, congestive heart failure, rheumatoid arthritis or inflammation.

DETAILED DESCRIPTION OF THE INVENTION

The present invention provides compounds of Formula I with affinity for steroid hormone nuclear receptors, particularly MR and/or GR, which could be used to modulate (i.e. repress, antagonize, agonize, partially antagonize, partially agonize) nuclear receptor activity and target gene expression, thereby influencing physiological functions related to steroid hormone levels and/or steroid hormone receptor activity. In this regard, compounds of Formula I are believed to be useful in treating or preventing a multitude of physiological disorders susceptible to steroid hormone nuclear receptor modulation. Thus, methods for the treatment or prevention of physiological disorders susceptible to steroid hormone nuclear receptor modulation constitute another important embodiment of the present invention. As a particular aspect, the present invention provides compounds useful as mineralocorticoid or glucocorticoid receptor modulators. As a more particular aspect, the present invention provides compounds useful as mineralocorticoid or glucocorticoid receptor antagonists.

As will be understood by the skilled artisan, some of the compounds useful for the methods of the present invention may be available for prodrug formulation. As used herein, the term "prodrug" refers to a compound of Formula I which has been structurally modified such that in vivo the prodrug is converted, for example, by hydrolytic, oxidative, reductive, or enzymatic cleavage, into the parent molecule ("drug") as given by Formula I. Such prodrugs may be, for example, metabolically labile ester derivatives of the parent compound where said parent molecule bears a carboxylic acid group. Conventional procedures for the selection and preparation of suitable prodrugs are well known to one of ordinary skill in the art. Conversely, some compounds of the present invention may be suitable as antedrugs. "Antedrugs" are themselves pharmacologically active agents, containing metabolically labile functional groups, that upon administration are subsequently deactivated in vivo. Lee et al., *Arch. Pharm. Res.,* 25(2); 111-136 (2002) provides a discussion of such antedrugs and their utility.

It is also understood that many of the steroid hormone nuclear receptor modulators of the present invention may exist as pharmaceutically acceptable salts and, as such, pharmaceutically acceptable salts are therefore included within the scope of the present invention. The term "pharmaceutically acceptable salt" as used herein, refers to salts of the compounds of Formula I, which are substantially non-toxic to living organisms. Typical pharmaceutically acceptable salts include those salts prepared by reaction of the compounds of the present invention with a pharmaceutically acceptable mineral or organic acid or an organic or inorganic base. Such salts are known as acid addition and base addition salts. It is further understood by the skilled reader that salt forms of pharmaceutical compounds are commonly used because they are often more readily crystallized, or more readily purified, than are the free bases. In all cases, the use of the pharmaceutical compounds of the present invention as salts is contemplated in the description herein. Hence, it is understood that where compounds of Formula I are capable of forming salts, the pharmaceutically acceptable salts and isoforms thereof are encompassed in the names provided herein.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, bromide, iodide, hydroiodide, dihydroiodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, hydroxybenzoate, methoxybenzoate, phthalate, xylenesulfonate, phenyl acetate, phenyl propionate, phenyl butyrate, citrate, lactate, α-hydroxybutyrate, glycolate, tartrate, methanesulfonate, propanesulfonate, naphthalene-1-sulfonate, napththalene-2-sulfonate, mandelate and the like. Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, anmmonium hydroxide, potassium carbonate, sodium carbonate, sodium bicarbonate, potassium bicarbonate, calcium hydroxide, calcium carbonate, and the like.

As used herein, the term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. In addition, two diastereomers which have a different configuration at only one chiral center are referred to herein as "epimers". The terms "racemate", "racemic mixture" or "racemic modification" refer to a mixture of equal parts of enantiomers.

The term "enantiomeric enrichment" as used herein refers to the increase in the amount of one enantiomer as compared to the other. A convenient method of expressing the enantiomeric enrichment achieved is the concept of enantiomeric excess, or "ee ", which is found using the following equation:

$$ee = \frac{E^1 - E^2}{E^1 + E^2} \times 100$$

wherein $E^1$ is the amount of the first enantiomer and $E^2$ is the amount of the second enantiomer. Thus, if the initial ratio of the two enantiomers is 50:50, such as is present in a racemic mixture, and an enantiomeric enrichment sufficient to produce a final ratio of 50:30 is achieved, the ee with respect to the first enantiomer is 25%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the enantiomers of compounds of Formula I can be resolved by one of ordinary skill in the art using standard techniques well known in the art, such as those described by J. Jacques, et al., "Enantiomers, Racemates, and Resolutions", John Wiley and Sons, Inc., 1981.

The compounds of the present invention may have one or more chiral centers and may, therefore, exist in a variety of stereoisomeric configurations. As a consequence of these chiral centers the compounds of the present invention may occur as racemates, mixtures of enantiomers, and as individual enantiomers as well as diastereomers and mixtures of diastereomers. All such racemates, enantiomers, and diastereomers are within the scope of the present invention. Enantiomers of the compounds provided by the present invention can be resolved, for example, by one of ordinary skill in the art using standard techniques such as those described by J. Jacques, et al., "Enantiomers, Racemates, and Resolutions", John Wiley and Sons, Inc., 1981.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond from the chiral carbon toward the lowest priority group. The term "S" (sinister) refers to that configuration of a chiral center with a counterclockwise relationship of group priorities (highest to second lowest) when viewed along the bond from the chiral carbon toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103-120.

The specific stereoisomers and enantiomers of compounds of Formula I can be prepared by one of ordinary skill in the art utilizing well known techniques and processes, such as those disclosed by Eliel and Wilen, "Stereochemistry of Organic Compounds", John Wiley & Sons, Inc., 1994, Chapter 7; Separation of Stereoisomers, Resolution, Racemization; and by Collet and Wilen, "Enantiomers, Racemates, and Resolutions", John Wiley & Sons, Inc., 1981. For example, specific stereoisomers and enantiomers can be prepared by stereospecific syntheses using enantiomerically and geometrically pure, or enantiomerically or geometrically enriched starting materials. In addition, the specific stereoisomers and enantiomers can be resolved and recovered by techniques such as chromatography on chiral stationary phases, enzymatic resolution or fractional recrystallization of addition salts formed by reagents used for that purpose.

In addition, as will be appreciated by one of ordinary skill in the art compounds of the present invention containing a carbon-carbon double bond may exist as geometric isomers. Two methods are commonly used to designate the specific isomers, the "cis-trans" method and the "E and Z" method, which methods designate a particular isomer based on whether the groups attached to each of the ethylene carbons are the same or different. A discussion of geometric isomerism and the naming of specific isomers is found in March, "Advanced Organic Chemistry", John Wiley & Sons, 1992, Chapter 4. All such geometric isomers, as well as mixtures of individual isomers, are contemplated and provided by the present invention.

As appreciated by one of ordinary skill in the art, suitable oxygen or nitrogen protecting groups are used as needed. Suitable oxygen or nitrogen protecting groups, as used herein, refers to those groups intended to protect or block the oxygen or nitrogen group against undesirable reactions during synthetic procedures. The suitability of the oxygen or nitrogen protecting group used will depend upon the conditions that will be employed in subsequent reaction steps wherein protection is required, and is well within the knowledge of one of ordinary skill in the art. Commonly used protecting groups suitable for practicing the present invention are disclosed in "Protective Groups in Organic Synthesis, 3$^{rd}$ Edition" by Theodara Greene, Peter G. M. Wuts, John Wiley & Sons, New York (1999).

As used herein the term "($C_1$-$C_4$)alkyl" refers to a straight or branched, monovalent, saturated aliphatic chain of 1 to 4 carbon atoms and includes, but is not limited to methyl, ethyl, n-propyl, isopropyl, n-butyl, isobutyl and the like.

As used herein the term "($C_1$-$C_6$)alkyl" refers to a straight or branched, monovalent, saturated aliphatic chain of 1 to 6 carbon atoms and includes, but is not limited to methyl, ethyl, n-propyl, isopropyl, n-butyl, isobutyl, t-butyl, n-pentyl, n-hexyl, and the like. It is understood that the term "$(C_1-C_4)$ alkyl" is included within the definition of "$(C_1-C_6)$alkyl".

As used herein the term "$(C_1-C_{10})$alkyl" refers to a straight or branched, monovalent, saturated aliphatic chain of 1 to 10 carbon atoms and includes, but is not limited to methyl, ethyl, propyl, isopropyl, n-butyl, isobutyl, tertiary butyl, pentyl, isopentyl, hexyl, 2,3-dimethyl-2-butyl, heptyl, 2,2-dimethyl-3-pentyl, 2-methyl-2-hexyl, octyl, 4-methyl-3-heptyl and the like. It is understood that the terms "$(C_1-C_4)$alkyl" and "$(C_1-C_6)$alkyl" are included within the definition of "$(C_1-C_{10})$ alkyl".

As used herein, the terms "Me", "Et", "Pr", "I-Pr", "Bu" and "t-Bu" refer to methyl, ethyl, propyl, isopropyl, butyl and tert-butyl respectively.

As used herein, the term "$(C_1-C_4)$alkoxy" refers to an oxygen atom bearing a straight or branched, monovalent, saturated aliphatic chain of 1 to 4 carbon atoms and includes, but is not limited to methoxy, ethoxy, n-propoxy, isopropoxy, n-butoxy, and the like. As used herein the term "$(C_1-C_6)$ alkoxy" refers to an oxygen atom bearing a straight or branched, monovalent, saturated aliphatic chain of 1 to 6 carbon atoms and includes, but is not limited to methoxy, ethoxy, n-propoxy, isopropoxy, n-butoxy, n-pentoxy, n-hexoxy, and the like. It is understood that the term "$(C_1-C_4)$alkoxy" is included within the definition of "$(C_1-C_6)$alkoxy".

As used herein, the term "hydroxy$(C_1-C_4)$alkyl" refers to a straight or branched, monovalent, saturated aliphatic chain of 1 to 4 carbon atoms bearing a hydroxyl group attached to one of the carbon atoms. As used herein, the term "hydroxy$(C_1-C_6)$alkyl" refers to a straight or branched, monovalent, saturated aliphatic chain of 1 to 6 carbon atoms bearing a hydroxyl group attached to one of the carbon atoms. It is understood that the term "hydroxy$(C_1-C_4)$alkyl" is included within the definition of "hydroxy$(C_1-C_6)$alkyl". As used herein, the term "hydroxy$(C_1-C_4)$alkoxy" refers to an oxygen atom bearing a straight or branched, monovalent, saturated aliphatic chain of 1 to 4 carbon atoms, further bearing a hydroxyl group attached to one of the carbon atoms. As used herein, the term "hydroxy$(C_1-C_6)$alkoxy" refers to an oxygen atom bearing a straight or branched, monovalent, saturated aliphatic chain of 1 to 6 carbon atoms, further bearing a hydroxyl group attached to one of the carbon atoms. It is understood that the term "hydroxy$(C_1-C_4)$alkoxy" is included within the definition of "hydroxy$(C_1-C_6)$alkoxy".

As used herein, the terms "halo", "halide" or "hal" of "Hal" refer to a chlorine, bromine, iodine or fluorine atom, unless otherwise specified herein.

As used herein, the term "halo$(C_1-C_4)$alkyl" refers to a straight or branched, monovalent, saturated aliphatic chain of 1 to 4 carbon atoms bearing one or more halo groups attached to one or more of the carbon atoms. As used herein, the term "halo$(C_1-C_6)$alkyl" refers to a straight or branched, monovalent, saturated aliphatic chain of 1 to 6 carbon atoms bearing one or more halo groups attached to one or more of the carbon atoms. It is understood that the term "halo$(C_1-C_4)$alkyl" is included within the definition of "halo$(C_1-C_6)$alkyl". As used herein, the term "halo$(C_1-C_4)$alkoxy" refers to an oxygen atom bearing a straight or branched, monovalent, saturated aliphatic chain of 1 to 4 carbon atoms, further bearing one or more halo groups attached to one or more of the carbon atoms. As used herein, the term "halo$(C_1-C_6)$alkoxy" refers to an oxygen atom bearing a straight or branched, monovalent, saturated aliphatic chain of 1 to 6 carbon atoms, further bearing one or more halo groups attached to one or more of the carbon atoms. It is understood that the term "halo$(C_1-C_4)$ alkoxy" is included within the definition of "halo$(C_1-C_6)$ alkoxy".

As used herein the term "$(C_2-C_6)$alkenyl" refers to a straight or branched, monovalent, unsaturated aliphatic chain having from two to six carbon atoms and having a double bond. Typical $(C_2-C_6)$alkenyl groups include ethenyl (also known as vinyl), 1-methylethenyl, 1-methyl-1-propenyl, 1-butenyl, 1-hexenyl, 2-methyl-2-propenyl, 1-propenyl, 2-propenyl, 2-butenyl, 2-pentenyl, and the like.

As used herein the term "$(C_2-C_6)$alkynyl" refers to a straight or branched, monovalent, unsaturated aliphatic chain having from two to six carbon atoms and having a triple bond. Typical $(C_2-C_6)$alkynyl groups include propynyl, ethynyl, and the like As used herein, the term "acyl" refers to a hydrogen or a $(C_1-C_6)$alkyl group attached to a carbonyl group. Typical acyl groups include formyl, acetyl, propionyl, butyryl, valeryl, and caproyl.

As used herein, the term "aryl" refers to a monovalent carbocyclic group containing one or more fused or non-fused phenyl rings and includes, for example, phenyl, 1- or 2-naphthyl, 1,2-dihydronaphthyl, 1,2,3,4-tetrahydronaphthyl, and the like As used herein the term "$(C_3-C_{10})$cycloalkyl" refers to a saturated hydrocarbon ring structure composed of one or more fused or unfused rings containing from three to ten carbon atoms. Typical $(C_3-C_{10})$cycloalkyl groups include cyclopropyl, cyclobutyl, cyclopentyl, cyclohexyl, cycloheptyl, cyclooctyl, adamantanyl, and the like. "$(C_3-C_7)$cycloalkyl" refers to a saturated hydrocarbon ring structure composed of one or more fused or unfused rings containing from three to seven carbon atoms. It is understood that the definition of "$(C_3-C_7)$cycloalkyl" is included within the definition of "$(C_3-C_{10})$cycloalkyl".

As used herein, the term "$(C_1-C_4)$alkyl-$(C_3-C_7)$cycloalkyl" refers to a straight or branched, monovalent, saturated aliphatic chain of 1 to 4 carbon atoms which has a $(C_3-C_7)$cycloalkyl attached to the aliphatic chain. Included within the term "$(C_1-C_4)$alkyl-$(C_3-C_7)$cycloalkyl" are the following:

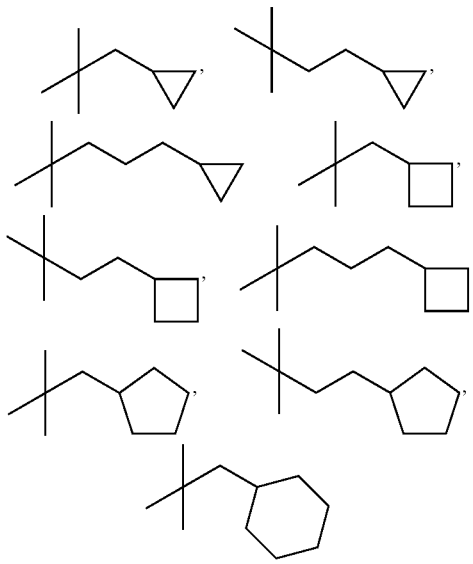

and the like.

As used herein, the term "$(C_1$-$C_4)$alkoxy-$(C_3$-$C_7)$cycloalkyl" refers to an oxygen atom bearing a straight or branched, monovalent, saturated aliphatic chain of 1 to 4 carbon atoms which has a $(C_3$-$C_7)$cycloalkyl attached to the aliphatic chain. Included within the term "$(C_1$-$C_4)$alkoxy-$(C_3$-$C_7)$cycloalkyl" are the following:

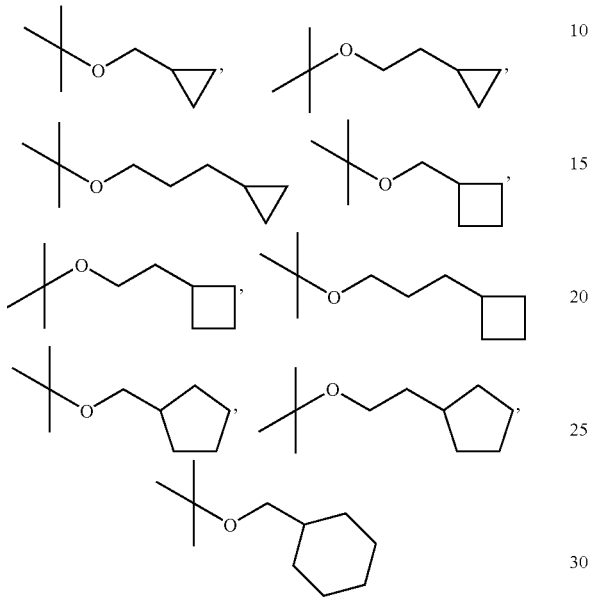

and the like.

As used herein the term "heterocycle" refers to a saturated or unsaturated, five- or six-membered ring, which contains one to four heteroatoms selected from the group consisting of oxygen, sulfur, and nitrogen. It is understood that the remaining atoms are carbon and that the heterocycle may be attached at any point which provides for a stable structure. Examples of heterocycle groups include thiophenyl, furanyl, tetrahydrofuryl, pyrrolyl, imidazolyl, pyrrazolyl, thiazolyl, thiazolidinyl, isothiazolyl, oxazolyl, isoxazolyl, triazolyl, thiadiazolyl, oxadiazolyl, tetrazolyl, pyridyl, pyridinyl, pyrimidyl, pyrazinyl, pyridiazinyl, triazinyl, imidazolyl, dihydropyrimidyl, tetrahydropyrimdyl, pyrrolidinyl, piperidinyl, piperazinyl, pyrazolidinyl, pyrimidinyl, imidazolidimyl, morpholinyl, pyranyl, thiomorpholinyl, and the like.

The term "substituted heterocycle" represents a heterocycle group substituted with one or two $(C_1$-$C_6)$alkyl moieties.

As used herein, the term "$(C_1$-$C_4)$alkyl-heterocycle" refers to a straight or branched, monovalent, saturated aliphatic chain of 1 to 4 carbon atoms which has a heterocycle group attached to the aliphatic chain. Examples of "$(C_1$-$C_4)$alkyl-heterocycle" include:

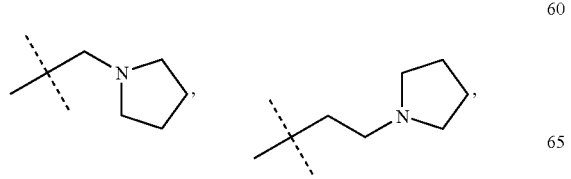

-continued

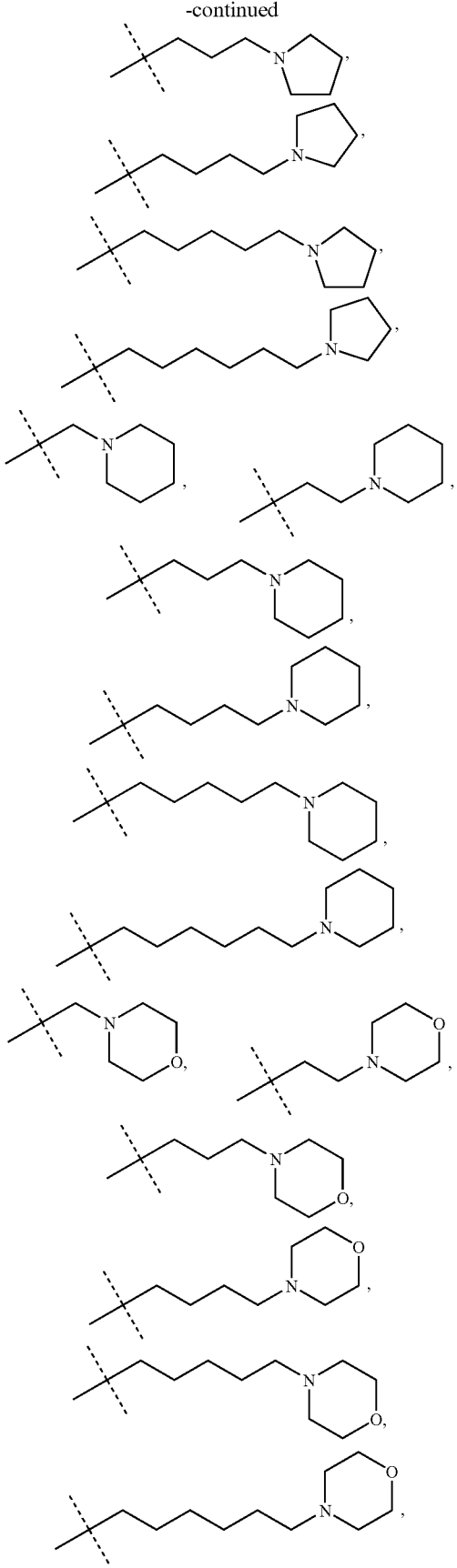

-continued

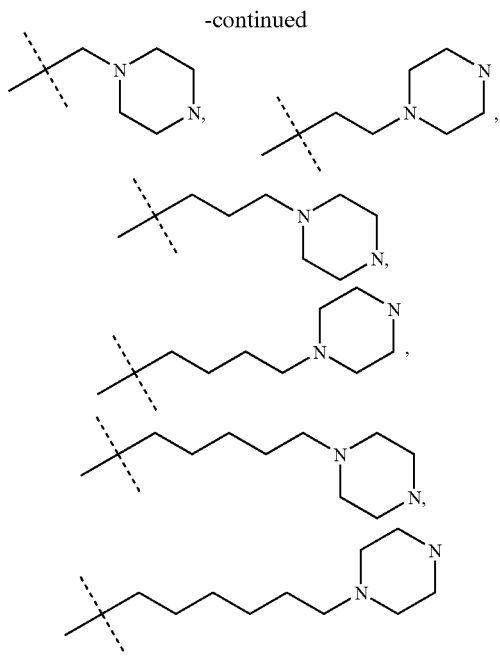

and the like.

The term "$(C_1-C_4)$alkyl-substituted heterocycle" refers to a straight or branched, monovalent, saturated aliphatic chain of 1 to 4 carbon atoms bearing a substituted heterocycle group as defined herein attached to the aliphatic chain.

As used herein, the term "NH—$(C_1-C_4)$ alkylamine" refers to a nitrogen atom substituted with a straight or branched, monovalent, saturated aliphatic chains of 1 to 4 carbon atoms. Included within the term "NH—$(C_1-C_4)$ alkylamine" are —NH(CH$_3$), —NH(CH$_2$CH$_3$), —NH(CH$_2$CH$_2$CH$_3$), —NH(CH$_2$CH$_2$CH$_2$CH$_3$), and the like.

As used herein the term "N,N—$(C_1-C_4)$dialkylamine" refers to a nitrogen atom substituted with two straight or branched, monovalent, saturated aliphatic chains of 1 to 4 carbon atoms. Included within the term "N,N—$(C_1-C_4)$dialkylamine" are —N(CH$_3$)$_2$, —N(CH$_2$CH$_3$)$_2$, —N(CH$_2$CH$_2$CH$_3$)$_2$, —N(CH$_2$CH$_2$CH$_2$CH$_3$)$_2$, —N,N(CH$_3$)(CH$_2$CH$_3$), —N,N(CH$_2$CH$_3$)(CH$_2$CH$_3$) and the like.

The designation " ▬ " refers to a bond that protrudes forward out of the plane of the page.

The designation " ⁞⁞⁞⁞ " refers to a bond that protrudes backward out of the plane of the page.

As used herein, the term "steroid hormone nuclear receptor modulator" refers to those nuclear hormone receptor ligands which bind to any one of GR, MR, AR, ER, or PR, of the larger class of nuclear hormone receptors, and either agonize, antagonize, partially agonize, or partially antagonize the receptor's activity.

As used herein the term "mineralocorticoid receptor" or "MR" refers to the mineralocorticoid receptor subtype, of the larger class of nuclear hormone receptors, which binds the mineralocorticoid hormone aldosterone, as its cognate ligand.

The term "mineralocorticoid receptor modulator" or "mineralocorticoid modulator" or "MR modulator" as used herein, refers to those nuclear hormone receptor ligands which bind to the mineralocorticoid receptor subtype and modulate (i.e. agonize, antagonize, partially agonize, or partially antagonize) the receptor activity. As a particular embodiment, the present invention provides antagonists of MR activity As used herein the term "glucocorticoid receptor" or "GR" refers to the glucocorticoid receptor subtype, of the larger class of nuclear hormone receptors, which binds the glucocorticoid hormones cortisol, corticosterone, or cortisone as its cognate ligand. The term "glucocorticoid receptor modulator" or "glucocorticoid modulator" or "GR modulator", as used herein, refers to those nuclear hormone receptor ligands which bind to the glucocorticoid receptor subtype and modulate (i.e. agonize, antagonize, partially agonize, or partially antagonize) the receptor activity.

As used herein, the term "disorder susceptible to steroid hormone nuclear receptor modulation" refers to any physiological disorder, of any origin, known or believed to be responsive to administration of a modulator (i.e. agonist, antagonist, partial agonist, or partial antagonist) of a steroid hormone nuclear receptor. Such disorders include Conn's Syndrome, primary and secondary hyperaldosteronism, increased sodium retention, increased magnesium and potassium excretion (diuresis), increased water retention, hypertension (isolated systolic and combined systolic/diastolic), arrhythmias, myocardial fibrosis, myocardial infarction, Bartter's Syndrome, disorders associated with excess catecholamine levels, diastolic and systolic congestive heart failure (CHF), peripheral vascular disease, diabetic nephropathy, cirrhosis with edema and ascites, esophageal varicies, Addison's Disease, muscle weakness, increased melanin pigmentation of the skin, weight loss, hypotension, hypoglycemia, Cushing's Syndrome, obesity, hypertension, glucose intolerance, hyperglycemia, diabetes mellitus, osteoporosis, polyuria, polydipsia, inflammation, autoimmune disorders, tissue rejection associated with organ transplant, malignancies such as leukemias and lymphomas, acute adrenal insufficiency, congenital adrenal hyperplasia, rheumatic fever, polyarteritis nodosa, granulomatous polyarteritis, inhibition of myeloid cell lines, immune proliferation/apoptosis, HPA axis suppression and regulation, hypercortisolemia, modulation of the Th1/Th2 cytokine balance, chronic kidney disease, stroke and spinal cord injury, hypercalcemia, hyperglycemia, acute adrenal insufficiency, chronic primary adrenal insufficiency, secondary adrenal insufficiency, congenital adrenal hyperplasia, cerebral edema, thrombocytopenia, and Little's syndrome, systemic inflammation, inflammatory bowel disease, systemic lupus erythematosus, discoid lupus erythematosus, polyartitis nodosa, Wegener's granulomatosis, giant cell arthritis, rheumatoid arthritis, osteoarthritis, hay fever, allergic rhinitis, contact dermatitis, atopic dermatitis, exfoliative dermatitis, urticaria, angioneurotic edema, chronic obstructive pulmonary disease, asthma, tendonitis, bursitis, Crohn's disease, ulcerative colitis, autoimmune chronic active hepatitis, hepatitis, cirrhosis, inflammatory scalp alopecia, panniculitis, psoriasis, inflamed cysts, pyoderma gangrenosum, pemphigus vulgaris, bullous pemphigoid, dermatomyositis, eosinophilic fasciitis, relapsing polychondritis, inflammatory vasculitis, sarcoidosis, Sweet's disease, type 1 reactive leprosy, capillary hemangiomas, lichen planus, erythema nodosum, acne, hirsutism, toxic epidermal necrolysis, erythema multiform, cutaneous T-cell lymphoma, psychoses, cognitive disorders (such as memory disturbances), mood disorders (such as depression and bipolar disorder), anxiety disorders, and personality disorders.

As used herein the term "congestive heart failure" (CHF) or "congestive heart disease" refers to a disease state of the cardiovascular system whereby the heart is unable to efficiently pump an adequate volume of blood to meet the requirements of the body's tissues and organ systems. Typically, CHF is characterized by left ventricular failure (systolic dysfunction) and fluid accumulation in the lungs, with the underlying cause being attributed to one or more heart or cardiovascular disease states including coronary artery disease, myocardial infarction, hypertension, diabetes, valvular heart disease, and cardiomyopathy. The term "diastolic congestive heart failure" refers to a state of CHF characterized by impairment in the ability of the heart to properly relax and fill with blood. Conversely, the term "systolic congestive heart failure" refers to a state of CHF characterized by impairment in the ability of the heart to properly contract and eject blood.

As appreciated by one of skill in the art, physiological disorders may present as a "chronic" condition, or an "acute" episode. The term "chronic", as used herein, means a condition of slow progress and long continuance. As such, a chronic condition is treated when it is diagnosed and treatment continued throughout the course of the disease. Conversely, the term "acute" means an exacerbated event or attack, of short course, followed by a period of remission. Thus, the treatment of physiological disorders contemplates both acute events and chronic conditions. In an acute event, compound is administered at the onset of symptoms and discontinued when the symptoms disappear. As described above, a chronic condition is treated throughout the course of the disease.

As used herein the term "patient" refers to a mammal, such a mouse, gerbil, guinea pig, rat, dog or human. It is understood, however, that the preferred patient is a human. As used herein, the terms "treating", "treatment", or "to treat" each mean to alleviate symptoms, eliminate the causation of resultant symptoms either on a temporary or permanent basis, and to prevent, slow the appearance, or reverse the progression or severity of resultant symptoms of the named disorder. As such, the methods of this invention encompass both therapeutic and prophylactic administration.

As used herein the term "effective amount" refers to the amount or dose of the compound, upon single or multiple dose administration to the patient, which provides the desired effect in the patient under diagnosis or treatment. An effective amount can be readily determined by the attending diagnostician, as one skilled in the art, by the use of known techniques and by observing results obtained under analogous circumstances. In determining the effective amount or dose of compound administered, a number of factors are considered by the attending diagnostician, including, but not limited to: the species of mammal; its size, age, and general health; the degree of involvement or the severity of the disease involved; the response of the individual patient; the particular compound administered; the mode of administration; the bioavailability characteristics of the preparation administered; the dose regimen selected; the use of concomitant medication; and other relevant circumstances.

A typical daily dose will contain from about 0.01 mg/kg to about 100 mg/kg of each compound used in the present method of treatment. Preferably, daily doses will be about 0.05 mg/kg to about 50 mg/kg, more preferably from about 0.1 mg/kg to about 25 mg/kg.

Oral administration is a preferred route of administering the compounds employed in the present invention whether administered alone, or as a combination of compounds capable of acting as a steroid hormone nuclear receptor modulator. Oral administration, however, is not the only route, nor even the only preferred route. Other preferred routes of administration include transdermal, percutaneous, pulmonary, intravenous, intramuscular, intranasal, buccal, sublingual, or intrarectal routes. Where the steroid hormone nuclear receptor modulator is administered as a combination of compounds, one of the compounds may be administered by one route, such as oral, and the other may be administered by the transdermal, percutaneous, pulmonary, intravenous, intramuscular, intranasal, buccal, sublingual, or intrarectal route, as particular circumstances require. The route of administration may be varied in any way, limited by the physical properties of the compounds and the convenience of the patient and the caregiver.

The compounds employed in the present invention may be administered as pharmaceutical compositions and, therefore, pharmaceutical compositions incorporating compounds of Formula I are important embodiments of the present invention. Such compositions may take any physical form that is pharmaceutically acceptable, but orally administered pharmaceutical compositions are particularly preferred. Such pharmaceutical compositions contain, as an active ingredient, an effective amount of a compound of Formula I, as described herein and above, including the pharmaceutically acceptable salts and hydrates thereof, which effective amount is related to the daily dose of the compound to be administered. Each dosage unit may contain the daily dose of a given compound, or may contain a fraction of the daily dose, such as one-half or one-third of the dose. The amount of each compound to be contained in each dosage unit depends on the identity of the particular compound chosen for the therapy, and other factors such as the indication for which it is given. The pharmaceutical compositions of the present invention may be formulated so as to provide quick, sustained, or delayed release of the active ingredient after administration to the patient by employing well known procedures. The following discussion provides typical procedures for preparing pharmaceutical compositions incorporating the compounds of the present invention. However, the following is in no way intended to limit the scope of the pharmaceutical compositions provided by the present invention.

Compositions are preferably formulated in a unit dosage form, each dosage containing from about 1 to about 500 mg of each compound individually or in a single unit dosage form, more preferably about 5 to about 300 mg (for example 25 mg). The term "unit dosage form" refers to a physically discrete unit suitable as unitary dosages for a patient, each unit containing a predetermined quantity of active material calculated to produce the desired therapeutic effect, in association with a suitable pharmaceutical carrier, diluent, or excipient.

The inert ingredients and manner of formulation of the pharmaceutical compositions are conventional. The usual methods of formulation used in pharmaceutical science may be used here. All of the usual types of compositions may be used, including tablets, chewable tablets, capsules, solutions, parenteral solutions, intranasal sprays or powders, troches, suppositories, transdermal patches and suspensions. In general, compositions contain from about 0.5% to about 50% of the compounds in total, depending on the desired doses and the type of composition to be used. The amount of the compound, however, is best defined as the "effective amount", that is, the amount of each compound which provides the desired dose to the patient in need of such treatment. The activity of the compounds employed in the present invention do not depend on the nature of the composition, hence, the compositions are chosen and formulated solely for convenience and economy.

Capsules are prepared by mixing the compound with a suitable diluent and filling the proper amount of the mixture in capsules. The usual diluents include inert powdered substances such as starches, powdered cellulose especially crystalline and microcrystalline cellulose, sugars such as fructose, mannitol and sucrose, grain flours, and similar edible powders.

Tablets are prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

Tablets are often coated with sugar as a flavor and sealant. The compounds may also be formulated as chewable tablets, by using large amounts of pleasant-tasting substances such as mannitol in the formulation, as is now well-established practice. Instantly dissolving tablet-like formulations are also now frequently used to assure that the patient consumes the dosage form, and to avoid the difficulty in swallowing solid objects that bothers some patients.

A lubricant is often necessary in a tablet formulation to prevent the tablet and punches from sticking in the die. The lubricant is chosen from such slippery solids as talc, magnesium and calcium stearate, stearic acid and hydrogenated vegetable oils.

Tablet disintegrators are substances which swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethylcellulose, for example, may be used, as well as sodium lauryl sulfate.

Enteric formulations are often used to protect an active ingredient from the strongly acid contents of the stomach. Such formulations are created by coating a solid dosage form with a film of a polymer which is insoluble in acid environments, and soluble in basic environments. Exemplary films are cellulose acetate phthalate, polyvinyl acetate phthalate, hydroxypropyl methylcellulose phthalate and hydroxypropyl methylcellulose acetate succinate.

When it is desired to administer the compound as a suppository, the usual bases may be used. Cocoa butter is a traditional suppository base, which may be modified by addition of waxes to raise its melting point slightly. Water-miscible suppository bases comprising, particularly, polyethylene glycols of various molecular weights are in wide use, also.

Transdermal patches have become popular recently. Typically they comprise a resinous composition in which the drugs will dissolve, or partially dissolve, which is held in contact with the skin by a film which protects the composition. Many patents have appeared in the field recently. Other, more complicated patch compositions are also in use, particularly those having a membrane pierced with innumerable pores through which the drugs are pumped by osmotic action.

It is understood by one of ordinary skill in the art that the procedures as described above can also be readily applied to a method of treating physiological disorders susceptible to steroid hormone nuclear receptor modulation, and particularly congestive heart failure.

Particular Aspects of the Compounds and Methods of the Invention

The following list sets out several groupings of particular substituents for compounds of Formula I. It will be understood that compounds of Formula I having such particular substituents, and the methods employing such compounds, represent particular aspects of the present invention. It will be further understood that each of these groupings of particular substituents may be combined with other provided groupings, to create still additional particular aspects of the compounds of the present invention Therefore, a particular aspect of the present invention is one wherein the compound of Formula I, is one wherein:

(a) Z represents S or O; and (b) Z represents S.

(c) Ar represents a group of the formula

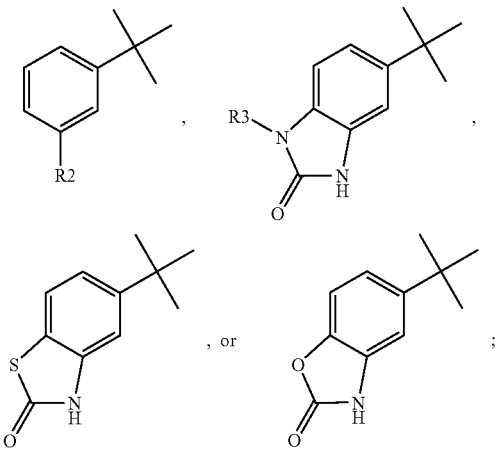

(d) Ar represents a group of the formula

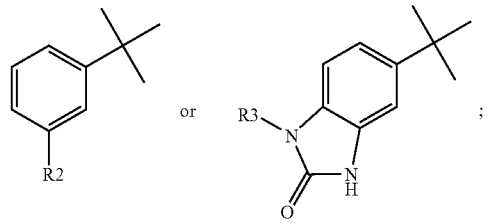

(e) Ar represents

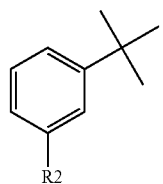

wherein $R^2$ represents hydroxy, $(C_1-C_6)$alkoxy, or NHSO$_2$R$^4$;

(f) Ar represents

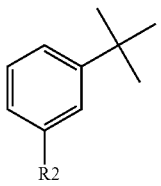

wherein R² represents hydroxy, methoxy, ethoxy, or NHSO₂R⁴;

(g) Ar represents

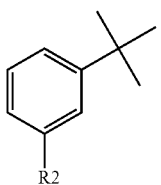

wherein R² represents NH SO₂R⁴;

(h) Ar represents

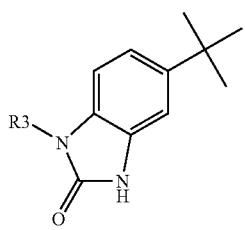

(i) Ar represents

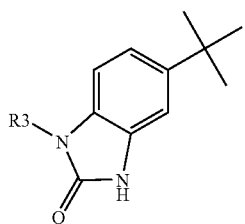

wherein R³ represents hydrogen, methyl, ethyl, isopropyl, heterocycle, substituted heterocycle, (C₁-C₄)alkyl-heterocycle, (C₁-C₄)alkyl-substituted heterocycle;

(j) Ar represents

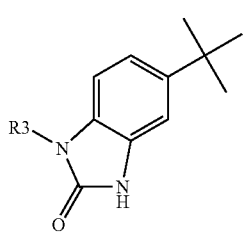

wherein R³ represents hydrogen, methyl, ethyl, or isopropyl;

(k) Ar represents

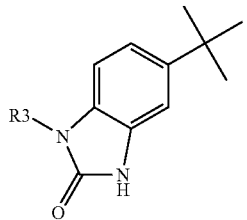

wherein R³ represents hydrogen, heterocycle, or substituted heterocycle;

(l) Ar represents

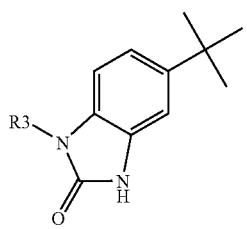

wherein R³ represents hydrogen, (C₁-C₄)alkyl-heterocycle, or (C₁-C₄)alkyl-substituted heterocycle;

(m) Ar represents

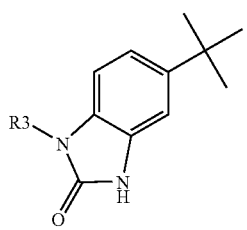

wherein R³ represents hydrogen or a group of the formula:

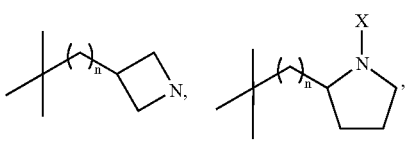

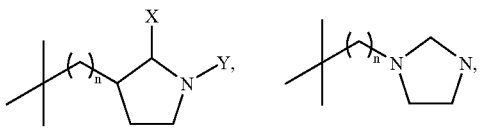

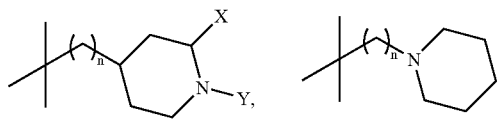

-continued

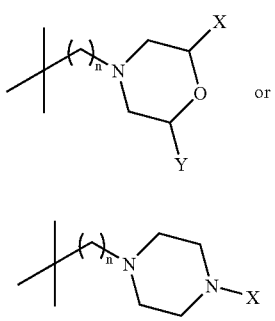 or wherein n represents 0-3 and X and Y each independently represent hydrogen, methyl or ethyl;

(n) Ar represents

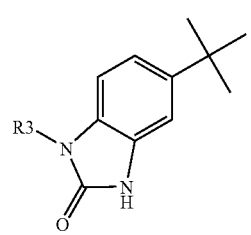

wherein R³ represents

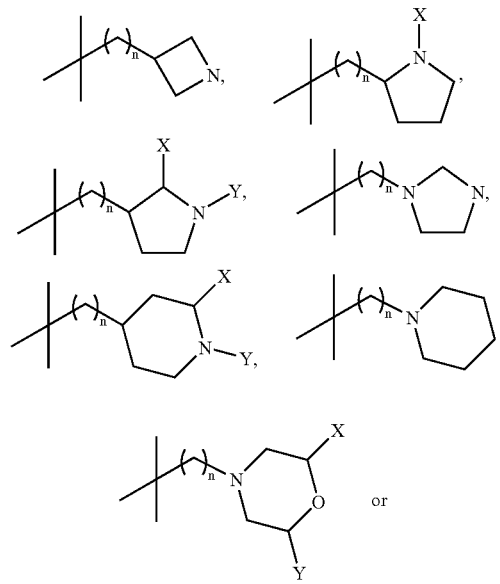

wherein n represents 0-3 and X and Y each independently represent hydrogen, methyl or ethyl;

(o) Ar represents

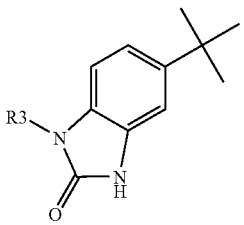

wherein R³ represents

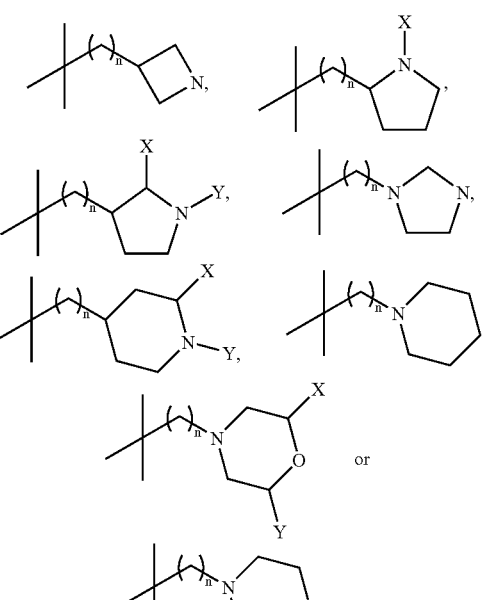

wherein n represents 0-3 and X and Y each independently represent methyl or ethyl;

(p) Ar represents

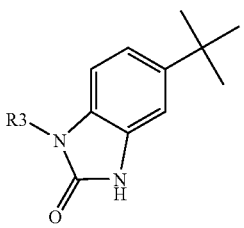

wherein R³ represents hydrogen or a group of the formula:

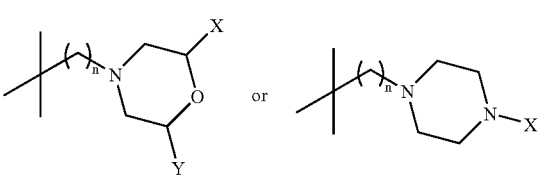

wherein n represents 0-2 and X and Y each independently represent hydrogen, methyl or ethyl;

(q) Ar represents

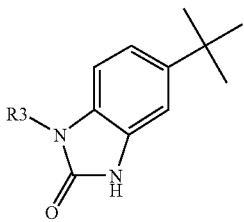

wherein $R^3$ represents hydrogen or a group of the formula:

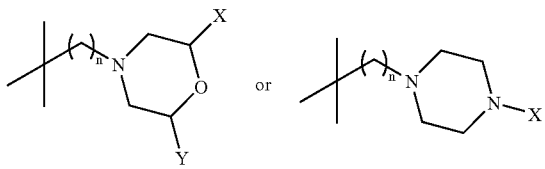

wherein n represents 2 and X and Y each independently represent hydrogen, methyl or ethyl;

(r) Ar represents

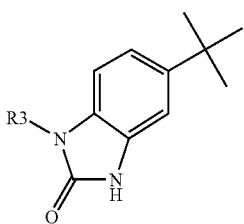

wherein $R^3$ represents hydrogen, $(C_1-C_6)$alkyl or a group of the formula:

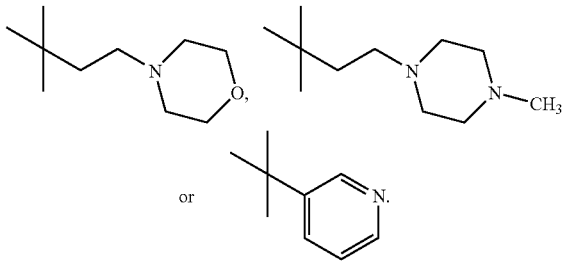

(s) $R^1$ represents hydrogen, methyl or ethyl; and
(t) $R^1$ represents hydrogen.
(u) $R^4$ represents independently at each occurrence methyl, ethyl, or propyl.
(v) $R^5$ and $R^6$ represent independently at each occurrence hydrogen, halo, hydroxy, halo$(C_1-C_6)$alkyl, $(C_1-C_6)$alkoxy, $(C_1-C_4)$alkyl-$(C_3-C_7)$cycloalkyl ,$(C_1-C_4)$alkoxy-$(C_3-C_7)$cycloalkyl, $NHR^7$, or $N(R^7)_2$;
(w) $R^5$ and $R^6$ represent independently at each occurrence hydrogen, fluoro, chloro, hydroxy, difluoromethyl, trifluoromethyl, $(C_1-C_6)$alkoxy,$(C_1-C_4)$alkyl-$(C_3-C_7)$cycloalkyl, $(C_1-C_4)$alkoxy-$(C_3-C_7)$cycloalkyl, $NHR^7$, or $N(R^7)_2$ wherein R7 represents independently at each occurrence $(C_1-C_6)$alkyl or $(C_3-C_7)$cycloalkyl;
(x) $R^5$ and $R^6$ represent independently at each occurrence hydrogen, fluoro, chloro, hydroxy, difluoromethyl, trifluoromethyl or $(C_1-C_6)$alkoxy;
(y) $R^5$ and $R^6$ represent independently at each occurrence hydrogen or fluoro; and
(z) $R^5$ and $R^6$ represent independently at each occurrence hydrogen.

In addition, it will be understood that a most particular aspect of the present invention is provided by each of the individual compounds exemplified herein. Compounds of Formula I can be chemically prepared, for example, by following the synthetic routes set forth in the Schemes below. However, the following discussion is not intended to be limiting to the scope of the present invention in any way. For example, the specific synthetic steps for the routes described herein may be combined in different ways, or with steps from different schemes, to prepare additional compounds of Formula I. Further, it should be recognized that the sequence in which the synthetic reactions take place is not implied and can be done in any fashion to achieve the desired final product. All substituents, unless otherwise indicated, are as previously defined. The reagents and starting materials are readily available to one of ordinary skill in the art. For example, certain reagents or starting materials can be prepared by one of ordinary skill in the art following procedures disclosed in *J. Heterocylic Chemistry,* 34 (2); 465 (1997) and Schulenberg, J. W., et al., *J. Org. Chem.,* 38; 1743 (1973).

Other necessary reagents and starting materials may be made by procedures which are selected from standard techniques of organic and heterocyclic chemistry, techniques which are analogous to the syntheses of known structurally similar compounds, and the procedures described in the Preparations and Examples below, including any novel procedures. In addition, one of ordinary skill will appreciate that many of the necessary reagents or starting materials can be readily obtained from commercial suppliers.

Compounds of Formula I, particularly where Z represents $CH_2$ may synthesized using procedures as descried in Scheme I.

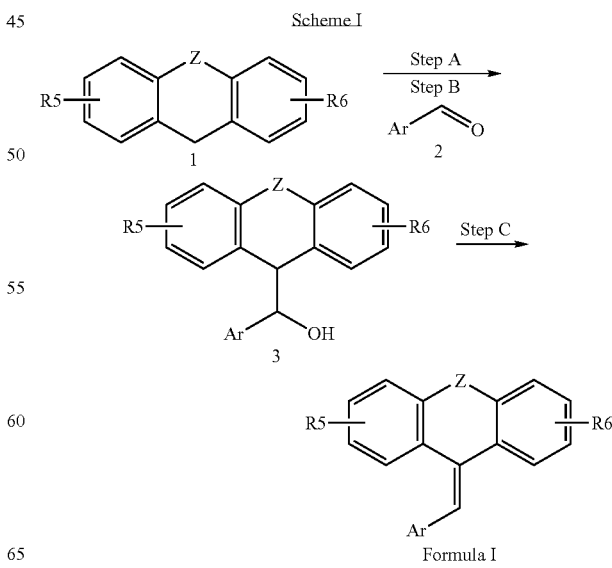

In Scheme I, Step A, the lithium anion of the dihydroanthracene derivative (1) (Z represents $CH_2$) is generated using an appropriate base such as n-buthyllithium, sec-butyllithium or t-butyllithium at −78° to 25° C. in an inert solvent such as THF, diethyl ether or diglyme for about 0.5-5 hours.

In Scheme I, Step B, after anion generation is complete, the reaction is cooled to about −25-10° C. and the benzaldehyde of structure (2) is added and the reaction is allowed to stir at room temperature for about 2-18 hours. The carbinol of structure (3) is isolated by removal of the solvent under reduced pressure and partitioning of the reaction between water and ethyl acetate. The crude carbinol (3) is used without further purification in Step C.

In Scheme I, Step C, the compound of structure (3) is dehydrated to a structure of Formula I by using 1-25% concentrated sulfuric acid in glacial acetic acid at 25-100° C. for 1 to 24 hours. The product is purified by standard techniques such as column chromatography on silica gel using ethyl acetate/hexanes mixtures.

Compounds of Formula I, particularly where Z represents O, may be synthesized according to procedures as described in Scheme II.

In Scheme II, Step A, the substituted xanthone (Z represents O) is mixed with an inert solvent such as diethyl ether, diglyme, THF or dioxane and added slowly to a solution of an excess of either methylmagnesium bromide or methyllithium in an inert solvent which has been cooled to about 10 to −78° C.

In Scheme II, Step B, after carbinol formation is complete, 4N HCl in dioxane is added carefully with cooling. The reaction is stirred at room temperature for about 0.5-24 hours. The reaction product of structure (5) is extracted into ethyl acetate, dried (magnesium sulfate) and concentrated. The crude product of structure (5) may be used in the next step without further purification or purified using standard techniques such as on silica gel using ethyl acetate/hexanes.

In Scheme II, Step C, structure (5) is dissolved in solvent such as carbon tetrachloride, chloroform, dichloromethane or 1,2-dichloroethane and treated with a slight excess of dimethylaminopyridine tribromide or bromine. The reaction is stirred at room temperature for about 1-24 hours. The excess brominating agent is quenched with sodium sulfite and the product extracted into an organic solvent. After drying (sodium sulfate) and concentration, the product is purified using standard techniques such as on silica gel using ethyl acetate/hexanes.

In Scheme II, Step D, the compounds of structures (6) and (7) are mixed in dioxane. Aqueous sodium carbonate is added and the container is sparged with nitrogen or argon for about 10 minutes. $(PhP)_4Pd$ is added and the reaction vessel is sealed immediately. The reaction is heated at about 70-100° C. for about 8-72 hours. The reaction is cooled and shaken with ethyl acetate/water. The organic layer is dried (magnesium sulfate) and concentrated. The product of Formula I may then be purified using standard techniques such as on silica gel using ethyl acetate/hexanes.

Alternatively, the intermediate of structure (5) may be synthesized according to the procedures as described in Scheme III, below.

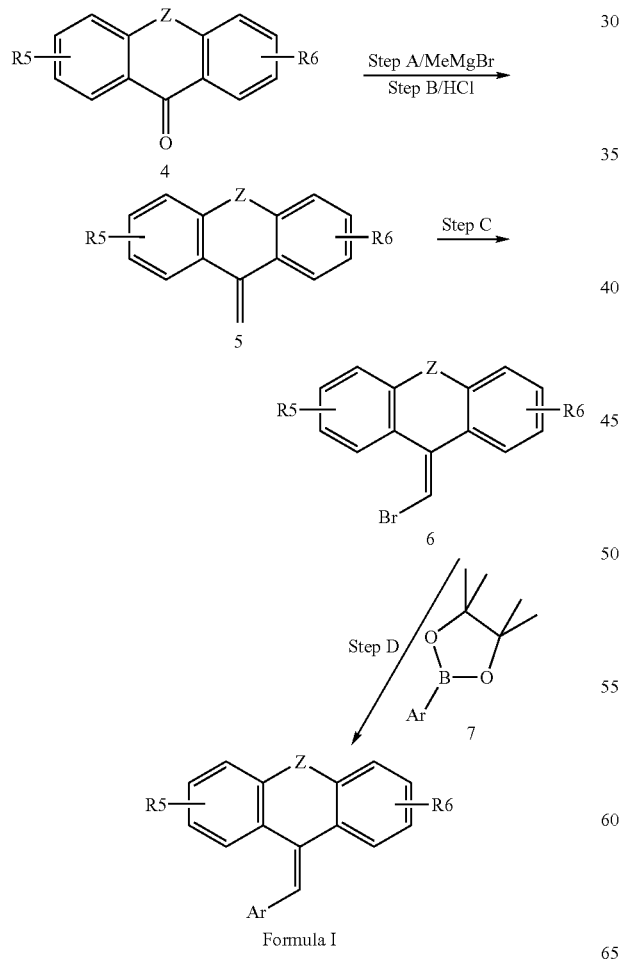

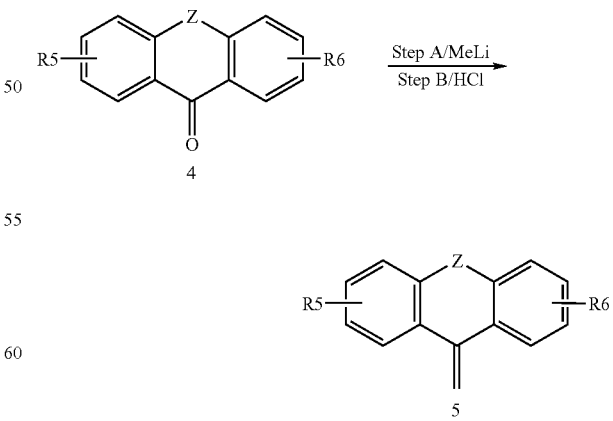

In Scheme III, Step A, a slurry of the compound of structure (4) is added to a chilled (0 to −45° C.) excess of methyllithium under nitrogen. After about 0.5-5 hours, the reaction is checked by HPLC to confirm that all of structure (4) has reacted. In Scheme III, Step B, the intermediate carbinol is cooled to about 0 to −25° C. and 4N HCl in dioxane is added slowly. The reaction is allowed to warm to room temperature and stirred for about 8 to 72 hours. The reaction is quenched with water and the product extracted into ethyl acetate. After drying the crude product of structure (5) may be used directly without further purification or purified using standard techniques such as on silica gel using ethyl acetate/hexanes.

The substituted or unsubstituted ketones of structure (4), where Z represents S, may be synthesized according to the procedures as described in Scheme IV, below.

standard techniques such as column chromatography on silica gel using 0 to 10% ethyl acetate in hexanes to give the pure product of structure (4).

Alternatively, the substituted ketones of structure (4) where Z represents S may be synthesized according to the general procedures as described in Scheme V, below.

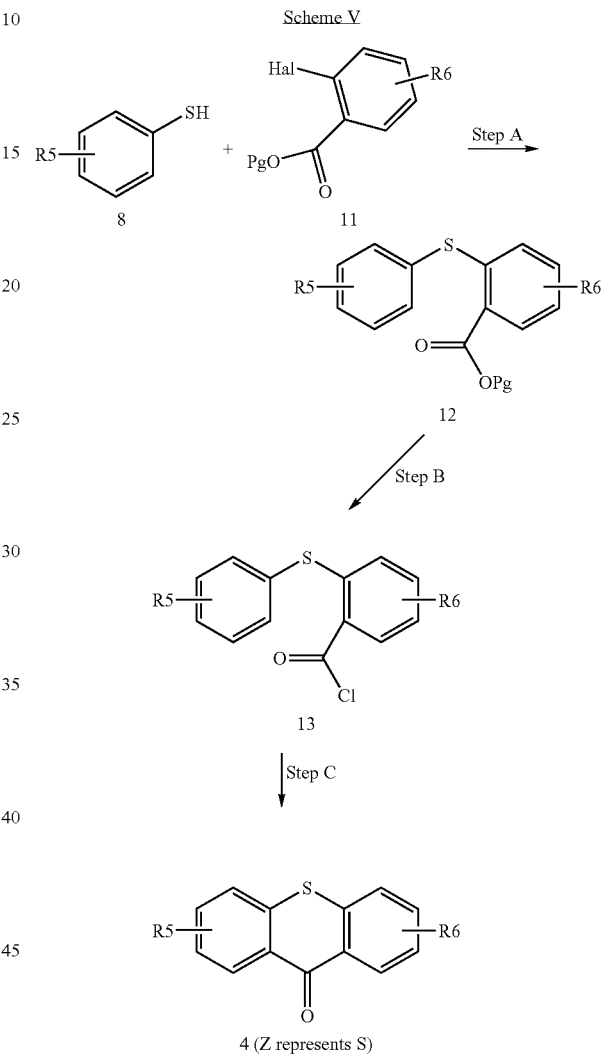

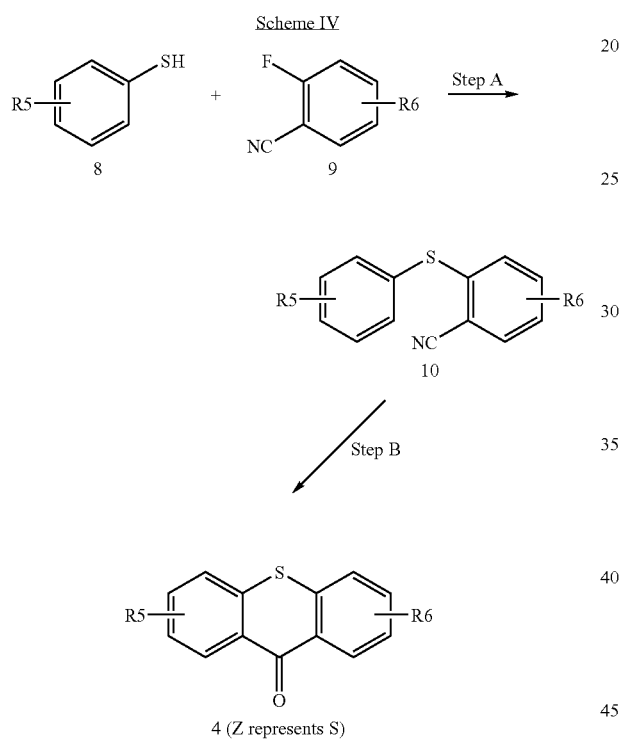

In Scheme IV, Step A, the sulfhydral of structure (8) is reacted with the fluoro nitrile of structure (9) using NaH in N,N-dimethylformamide (J Heterocylic Chemistry, 34 (2) 465 (1997)) or potassium carbonate in THF. The reaction is stirred at about 25-75° C. for about 4-24 hours. The reaction is shaken with water/ethyl acetate, dried (magnesium sulfate) and concentrated to give the crude compound of structure (10). The product may then be purified by standard techniques such as column chromatography on silica gel using 0 to 10% ethyl acetate in hexanes to give the pure product of structure (10).

In Scheme IV, Step B, the compound of structure (10) is mixed with about 2 to 25 equivalents by weight of polyphosphoric acid (PPA). The reaction is heated at about 150-230° C. for about 18-120 hours. After cooling the reaction is diluted with water and ethyl acetate. This mixture may then be filtered through a bed of Celite and then further purified by Briefly, in Scheme V, Step A, the aryl sulfhydryl of structure (8) is alkylated with an aryl halide of structure (11) (where Hal represents Br or Cl) in an inert solvent, such as DMF, CHCl, and the like, in the presence of a strong organic or inorganic base, such as NaOH, NaH, t-BuLi, and the like, at ambient or elevated temperatures. In Scheme V, Step B, the carbonyl of structure (12) is activated using standard techniques, such as treatment with an acid chloride to provide the compound of structure (13). Finally, in Scheme V, Step C, the compound of structure (13) is cyclized using standard techniques, such as the commonly known Friedel-Craft's conditions.

9-alkenyl substituted intermediate compounds of structure (15) may be synthesized according to procedures as provided generally in Scheme VI, below.

Scheme VI

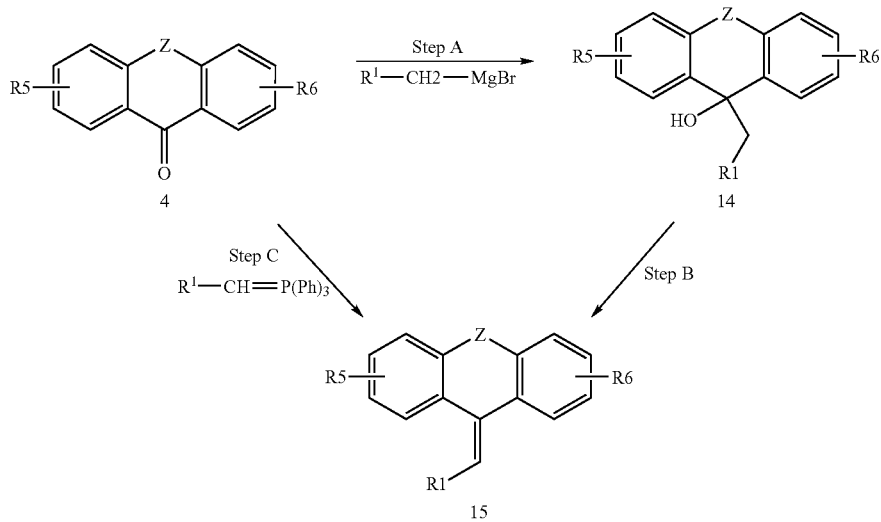

Briefly, In Scheme VI, Step A, the compound of structure (4) is treated with an organo metallic reagent, such as a Grinard reagent, alky or aryl lithium, and the like, to form the substituted tertiary hydroxy compound of structure (14). In Scheme VI, Step B, the tertiary alcohol of structure (14) is dehydrated under acidic conditions to form the alkylene of structure (15). Alternately, in Step C, compound of structure (4) may be treated with the appropriate Wittig reagent to form compounds of structure (15) directly.

As an alternative to Scheme II, compounds of Formula I, particularly where R1 represents an alkyl group, can be synthesized according to procedures as generally described in Scheme VII, below.

Scheme VII

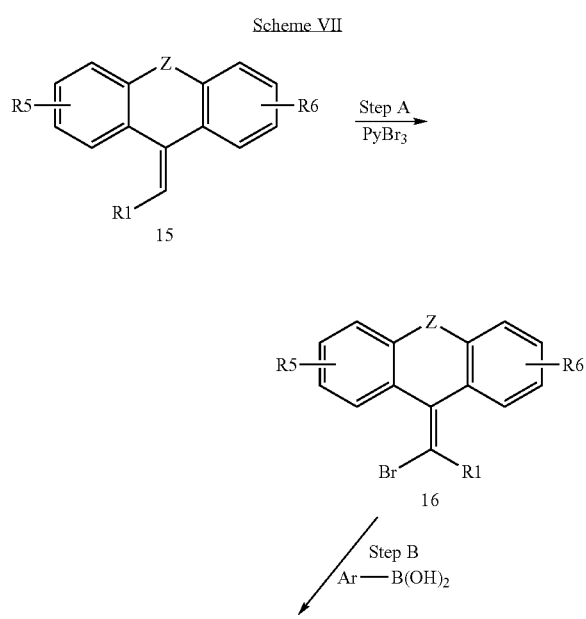

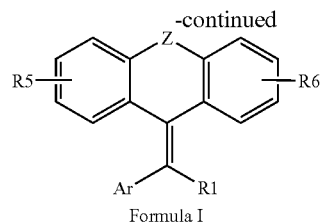

Formula I

Briefly, in Scheme VII, Step A, the double bond of structure (15) is activated via bromination using a suitable brominating agent such as bromine, pyridine tribromide, dimethylaminopyridine tribormide, and the like, at a suitable temperature in an inert solvent, such as $CH_2Cl_2$ or methylene chloride. In Step B, arylation of structure (16) is accomplished by a coupling reaction of an appropriate substituted phenyl boronic acid or borate ester with the vinyl bromide of structure (16) using a metallic catalyst reagent, such as tetrakis(triphenylphosphine)Pd(0), in the presence of a base such sodium carbonate at elevated temperature. Finally, the compound of Formula I may then be concentrated and purified using standard techniques.

Determination of Biological Activity:

To demonstrate that compounds of the present invention have affinity for steroid hormone nuclear receptors, and thus have the capacity to modulate steroid hormone nuclear receptors, soluble MR and GR binding assays are performed. All ligands, radioligands, solvents, and reagents employed in the binding assays are readily available from commercial sources, or can be readily synthesized by the ordinarily skilled artisan.

Mineralocorticoid Receptor Binding Assay (Method 1):

The full length human MR gene is cloned from a human kidney or human brain cDNA library. Briefly, using synthetic oligonucleotide primers (Eli Lilly and Company, Indianapolis) directed to nucleotides 20-54 and 3700-3666 of the human MR, polymerase chain reaction (PCR) is performed under standard conditions using a human cDNA library. The PCR reaction is performed in a final volume of 50 µl containing about 1µl of a 50× stock solution of polymerase; about 1 µl of a 50× stock solution of dNTP; about 5µl of an appropriate PCR buffer; about 1 µl of each primer; about 5 µl of a H. kidney or H. brain cDNA library; and about 36 µl of water. The reaction is allowed to denature for about 30 seconds at 95 degrees Celsius, anneal for about 30 seconds at 55 degrees Celsius, and extend for about 5 minutes at 72 degrees Celsius, the sequence being repeated for a total of about 35 cycles. The desired PCR product (3.68 Kb) is confirmed by gel electrophoresis and subsequently cut from the gel and stored at about −20 degrees Celsius until extraction. To extract the cDNA product from the agarose gel, the QIAEX II Gel Extraction protocol (QIAGEN, Inc.) is employed according to the manufacturer's instructions. Following extraction, the MR cDNA is cloned into an appropriate cloning vector (Zero Blunt TOPO PCR Cloning Kit (Invitrogen, Inc.) and a pAcHLT-baculovirus transfer vector (B.D./Pharminogen), then expressed in SF9 insect cells, essentially according to manufacturer's instructions. Sf9 cells are grown at a scale where gram quantity cell pellets are obtained for subsequent use in the MR binding assay. Harvested cell pellets are lysed by repeated freeze-thaw cycles (about 4) in a suitable lysis buffer then centrifuged at about $1 \times 10^3 G$ (with the supernatant being saved for future assays).

MR binding assays are performed in a final total volume of about 250 µl containing about 20-25 µg of protein and 0.5 nM of [$^3$H]-aldosterone plus varying concentrations of test compound or vehicle. The assay binding buffer consists of 30 mM sodium molybdate, 30 mM of TRIS-HCl, 5 mM sodium phosphate, 5 mM sodium pyrophosphate, and about 10% glycerol, pH=7.5.

Briefly, assays are prepared at RT in 96-well Falcon 3072 plates, each well containing 210 µof binding buffer, 10 µl of [$^3$1H]-aldosterone, 10 µl of test compound/vehicle, and 20 µl of the resuspended receptor protein extract. Incubations are carried out at 4 degrees Celsius with shaking for about 16 hours. 200 µl aliquots of each incubation are filtered onto Millipore HA 0.45 micron 96-well filter plates, pre-moistened with cold 30 mM TRIS-HCl. The filter plates are suctioned dry with vacuum and immediately washed 3× with cold 30 mM TRIS-HCl. The plates are then punched out and the amount of receptor-ligand complex is determined by liquid scintillation counting using 4 ml of Ready Protein Plus™ liquid scintillation cocktail.

IC$_{50}$ values (defined as the concentration of test compound required to decrease [$^3$H]-aldosterone binding by 50%) are then determined. Ki values for each respective test compound can then be calculated by application of the Cheng-Prusoff equation as described in Cheng et al., Relationship Between The Inhibition Constant (Ki) and The Concentration of Inhibitor Which Causes 50% Inhibition (IC$_{50}$) of an Enzymatic Reaction, Biochem. Pharmacol., 22: 3099-31088; (1973).

Glucocorticoid Receptor Binding Assay (Method 1):

To demonstrate the GR modulating potency of compounds of the present invention the following source of glucocorticoid receptor is employed. A549 human lung epithelial cells (ATCC) are grown at a scale where gram quantity cell pellets are obtained. Harvested cell pellets are washed twice in cold phosphate buffered saline, centrifuged, and resuspended in cold assay binding buffer. The assay binding buffer consists of 10% glycerol, 50 mM Tris-HCl (pH7.2), 75 mM sodium chloride, 1.5 mM magnesium chloride, 1.5 mM EDTA, and 10 mM sodium molybdate. Cell suspensions were lysed via sonication, centrifuged, and the "extract" supernatant is snap frozen and stored at −80 C. until needed.

GR binding assays are performed in a final volume of 140 ul containing 50-200 ug of A549 cell extract and 1.86 nM [$^3$H]-dexamethasone (Amersham) plus varying concentrations of test compound or vehicle. Briefly, assays are prepared at RT in 96-well Fisher 3356 plates, each well containing 100 ul of A549 cell extract, 20 ul of [$^3$H]-dexamethasone, and 20 ul of test compound/vehicle. Incubations are carried out at 4 degrees Celsius for 16 hours. After incubation, 70 ul of 3× dextran-coated charcoal solution is added to each reaction, mixed, and incubated for 8 minutes at RT. 3×-dextran-coated charcoal solution consists of 250 ml assay binding buffer, 3.75 g Norit A charcoal (Sigma), and 1.25 g dextran T-70 (Amersham). Charcoal/unbound radioligand complexes are removed by centrifugation of the plate and 140 ul of supernatant from each well is transferred to another 96 well Optiplate (Packard Instruments). 200 ul of Microscint-20 scinillant (Packard Instruments) is added to each well and amount of receptor bound radioligand is determined using Packard Instruments TopCount instrument.

IC$_{50}$ values, defined as the concentration of test compound required to decrease [$^3$H]-dexamethasone binding by 50%, are then determined. Ki values for each respective test compound can then be calculated by application of the Cheng-Prusoff equation as described in Cheng et al., Relationship Between The Inhibition Constant (Ki) and The Concentration of Inhibitor Which Causes 50% Inhibition (IC$_{50}$) of an Enzymatic Reaction, Biochem. Pharmacol., 22: 3099-31088; (1973).

Alternative Binding Assay Protocol for MR, GR, AR, and PR (Method 2):

Cell lysates from 293 cells overexpressing human GR (glucocorticoid receptor), AR (androgen receptor), MR (mineralocorticoid receptor) or PR (progesterone receptor) are used for competition binding assays to determine Ki values for test compounds. Briefly, competition binding assays are run in a buffer containing 20 mM Hepes, pH 7.6, 0.2 mM EDTA, 75 mM NaCl, 1.5 mM MgCl2, 20% glycerol, 20 mM sodium molybdate, 0.2 mM DTT, 20 ug/ml aprotinin and 20 ug/ml leupeptin, using either 0.3 nM $^3$H-dexamethasone for GR binding, 0.36 nM $^3$H-methyltrienolone for AR binding, 0.25 nM $^3$H-aldosterone for MR binding, or 0.29 nM $^3$H-methyltrienolone for PR binding, and either 20 ug 293-GR lysate, 22 ug 293-AR lysate, 20 ug 293-MR lysate or 40 ug 293-PR lysate per well. Competing compounds are added various concentrations in half-log increments. Non-specific binding is determined in the presence of 500 nM dexamethasone for GR binding, 500 nM aldosterone for MR binding, or 500 nM methyltrienolone for AR and PR binding. The binding reaction (140 µl) is incubated for overnight at 4° C. then 70 µl of cold charcoal-dextran buffer (containing per 50 ml of assay buffer, 0.75 g of charcoal and 0.25 g of dextran) is added to each reaction. Plates are mixed 8 minutes on an orbital shaker at 4° C. Plates are then centrifuged at 3,000 rpm at 4° C. for 10 minutes. An aliquot of 120 µl of the mix is transferred to another 96-well plate and 175 µl of Wallac Optiphase "Hisafe 3" scintillation fluid is added to each well. Plates are sealed and shaken vigorously on an orbital shaker. After an incubation of 2 hrs, plates are read in a Wallac Microbeta counter. The data is used to calculate an IC$_{50}$ and % Inhibition at 10 µM. The K$_d$ for $^3$H-dexamethasone for GR binding, $^3$H-methyltrienolone for AR binding, $^3$H-aldosterone for MR binding, or $^3$H-methyltrienolone for PR binding, is determined by saturation binding. The IC$_{50}$ values for compounds are converted to $K_i$ using Cheng-Prusoff equation and the $K_d$ determined by saturation binding assay.

Binding assay protocols for steroid hormone nuclear receptors similar to those described above can be readily designed by the ordinarily skilled artisan. U.S. Pat. No. 6,166,013 provides examples of such protocols. Representative compounds of the present invention have a Ki in the MR or GR binding assay of ≦50 µM. Table I (see below) provides MR and GR binding data for a representative sample of the exemplified compounds of the present invention.

To demonstrate the ability of compounds of the present invention to modulate the activity of a steroid hormone nuclear receptor (i.e. either agonize, antagonize, partially agonize, or partially antagonize), bioassays are performed which detect modulation of target gene expression in cells transiently transfected with a nuclear receptor protein and a hormone response element-reporter gene construct. The solvents, reagents, and ligands employed in the functional assay are readily available from commercial sources, or can be synthesized by one of ordinary skill in the art.

Functional Assay of Mineralocorticoid Receptor Modulation (Method 1):

For the MR transient transfection assay, COS-7 cells are transfected with full length human MR and a 2×GRE-luciferase gene construct. Following transfection, the ability of test compounds to modulate expression of the luciferase reporter gene product is monitored. Briefly, on day one, COS cells are harvested from cell culture plates using standard procedures such as treatment with Trypsin-EDTA (GIBCO BRL). Culture medium is then added to the cells and the cell-medium mixture is plated in 96-well plates coated with poly-(d)-lysine (approximately 3×10$^4$ cells/well). Cells are grown for about 4 hours then transfected with Fugene-6 reagent with plasmids containing human MR, previously cloned into pc.DNA 3.1 expression vector, and 2×GRE-reporter gene construct (GRE-luciferase), previously cloned into pTAL-luc vector. Transfection is carried out in DMEM with 5% fetal calf serum, charcoal treated. 24 hours later cells are exposed to various concentrations of aldosterone in the presence and absence of test compound and incubated for an additional 24 hours. The reaction is terminated by the addition of lysis buffer followed by luciferin (luciferase substrate). Luciferase expression, as an indicator of ligand induced MR transactivation, is monitored by chemiluminescence measured using a microtiter plate luminometer (MLX). The kinetic inhibition constant ($K_b$ or $K_p$) can then be determined by analysis of dose-response curves for aldosterone, in the presence and absence of test compound, using standard techniques.

Alternative Functional Assay for MR, GR, PR, and AR Activity (Method 2):

Human embryonic kidney hEK293 cells are co-transfected using Fugene. Briefly, the reporter plasmid containing two copies of GRE (glucocorticoid response element $^5$'TGTA-CAGGATGTTCT$^{3'}$) and TK promoter upstream of the luciferase reporter cDNA, is transfected with a plasmid constitutively expressing either human glucocorticoid receptor (GR), human mineralocorticoid receptor (MR), or human progesterone receptor (PR), using viral CMV promoter. The reporter plasmid containing two copies of probasin ARE (androgen response element $^5$'GGTTCTTGGAGTACT$^{3'}$) and TK promoter upstream of the luciferase reporter cDNA, is transfected with a plasmid constitutively expressing human androgen receptor (AR) using viral CMV promoter. Cells are transfected in T150 cm$^2$ flasks in DMEM media with 5% charcoal-stripped Fetal Bovine Serum (FBS). After a overnight incubation, transfected cells are trypsinized, plated in 96 well dishes in DMEM media containing 5% charcoal-stripped FBS, incubated for 4 h and then exposed to various concentrations of test compounds in half log increments. In the antagonist assays low concentrations of agonist for each respective receptor are added to the media (0.25 nM dexamethosone for GR, 0.3 nM of methyltrienolone for AR, 0.05 nM of progesterone for PR and 0.05 nM aldosterone). After 24 h of incubations with compounds, cells are lysed and luciferase activity is determined. Data is fit to a 4 parameter-fit logistics to determine EC50 values. The % efficacy is determined versus maximum stimulation obtained with 100 nM methyltrienolone for AR assay, with 30 nM progesterone for PR assay, with 30 nM aldosterone for MR assay and with 100 nM dexametasone for GR assay.

TABLE I

Mineralocorticoid and Glucocorticoid Receptor Binding Assay Values

| Example No. | MR Ki (nM) Method 1 | GR Ki (nM) Method 1 | GR Ki (nM) Method 2 |
|---|---|---|---|
| 1 | +++ | -- | |
| 2 | +++ | | +++ |
| 3 | +++ | | +++ |
| 4 | +++ | | +++ |
| 5 | +++ | | ++ |
| 6 | +++ | | +++ |
| 7 | +++ | | +++ |
| 8 | +++ | | +++ |
| 9 | +++ | | ++ |
| 10 | +++ | | + |
| 11 | +++ | | +++ |
| 12 | +++ | | +++ |
| 13 | +++ | | ++ |
| 14 | +++ | | + |
| 15 | +++ | | +++ |
| 16 | +++ | | -- |
| 17 | +++ | | -- |
| 18 | +++ | + | |
| 19 | +++ | + | |
| 20 | +++ | ++ | |

Legend:
"+" represents a value of ≦10,000 nM
"++" represents a value of ≦1,000 nM
"+++" represents a value of ≦500 nM
"--" indicates the value was not determined The following Preparations and Examples further illustrate the invention and represent typical syntheses of the compounds of Formula I, including any novel compounds, as described generally in the Schemes above. The reagents and starting materials are readily available from commercial suppliers or may be readily synthesized by one of ordinary skill in the art following the general procedures as described herein. Where the synthesis of the compound is not explicitly stated, a reference to a previous Example or representative Scheme describing procedures for the synthesis of the compound is provided. It should be understood that the Preparations and Examples are set forth by way of illustration and not limitation, and that various modifications may be made by one of ordinary skill in the art.

As used herein, the following terms have the meanings indicated: "i.v." refers to intravenously; "p.o." refers to orally; "i.p." refers to intraperitoneally; "eq" or "equiv." Refers to equivalents; "g" refers to grams; "mg" refers to milligrams; "L" refers to liters; "mL" refers to milliliters; "µL" refers to microliters; "mol" refers to moles; "mmol" refers to millimoles; "psi" refers to pounds per square inch; "mm Hg" refers to millimeters of mercury; "min" refers to minutes; "h" or "hr" refers to hours; "° C." refers to degrees Celsius; "TLC"

refers to thin layer chromatography; "HPLC" refers to high performance liquid chromatography; "$R_f$" refers to retention factor; "$R_t$" refers to retention time; "δ" refers to part per million down-field from tetramethylsilane; "THF" refers to tetrahydrofuran; "DTMF" refers to N,N-dimethylformamide; "DMSO" refers to dimethyl sulfoxide; "aq" refers to aqueous; "EtOAc" refers to ethyl acetate; "iPrOAc" refers to isopropyl acetate; "MeOH" refers to methanol; "MTBE" refers to tert-butyl methyl ether; "$PPh_3$" refers to triphenylphosphine; "DEAD" refers to diethyl azodicarboxylate; "RT" refers to room temperature; "Pd—C" refers to palladium over carbon; "SAX" refers to strong anion exchange; "SCX" refers to strong cation exchange; $NaBH(Oac)_3$ refers to sodium triacetoxyborohydride; "Bn" refers to benzyl; "$BnNH_2$" refers to benzyl amine; m-CPBA refers to meta-chloroperoxybenzoic acid; $H_2$ refers to hydrogen; "$K_i$" refers to the dissociation constant of an enzyme-antagonist complex and serves as an index of ligand binding; and "$ID_{50}$" and "$ID_{100}$" refer to doses of an administered therapeutic agent which produce, respectively, a 50% and 100% reduction in a physiological response.

Instrumental Analysis:

Unless otherwise indicated, $^1$H NMR spectra are recorded on a either a 300 MHz or 400 MHz Varian spectrometer at ambient temperature. Data are reported as follows: chemical shift in ppm from internal standard tetramethylsilane on the δ scale, multiplicity (b=broad, s=singlet, d=doublet, t=triplet, q=quartet, qn=quintet and m=multiplet), integration, coupling constant (Hz) and assignment. Positive and negative electrospray mass spectral data are obtained on a Micromass Platform LCZ equipped with an autosampler. Analytical thin layer chromatography is performed on EM Reagent 0.25-mm silica gel 60-F plates. Visualization is accomplished with UV light. HPLC analysis is performed on an Agilent 1100 Series HPLC using an acetonitrile/0.03M phosphate buffer (80/20) as the mobile phase using an Agilent Eclipse XDB-C8 analytical 4.6×150 mm 5-micron column. Melting points are determined on a Mettler Toledo FP62 melting point apparatus. GC-MS data are obtained on an Agilent HP6890 GC using a HP-5MS (30 m, 0.25 mm i.d., 0.25 μm film) column.

Compounds where Z represents S

Preparation 1

9-Hydroxy-9-methylthioxanthine

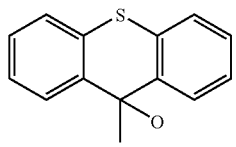

Prepare solution by dissolving 2.12 g (10 mmol) of thioxanthone in 50 mL of anhydrous THF. Add a solution of 5 mL of 3M methylmagnesium bromide in THF (15 mmol) and stir the reaction at ambient temperature. Allow the reaction to proceed for sixteen hours. Quench the reaction with the addition of 1N HCl and add 50 mL of EtOAc. Separate the organic layer and dry by filtration through anhydrous $Na_2SO_4$. Remove the volatiles by evaporation in vacuo. Isolate this product (1.77 g) as a brown oil and use in subsequent reactions without further purification.

Preparation 2

9-Methylenethioxanthine

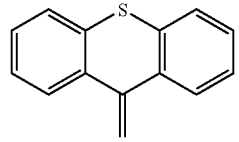

Dissolve all of the product from Preparation 1 in 25 mL of glacial acetic acid and add 1 mL of concentrated sulfuric acid. Attach a drying tube to the reaction vessel. Stir the reaction and allow to proceed for sixteen hours at ambient temperature. Reduce the reaction volume by evaporation, and quench the reaction with the addition of water. Extract the reaction mixture with EtOAc and separate the organic layer. Wash the EtOAc extract with a saturated aqueous solution of sodium carbonate, follow with an extraction with water, and finally dry with anhydrous $Na_2SO_4$ and evaporate to an oil. Purify the resulting crude product by chromatography on silica gel eluted with Hexane-EtOAc(4:1 v/v). Collect the appropriate fractions and evaporate to dryness. This procedure yields 370 mg of the title compound as a tan amorphous powder, with the following physical chemical characteristics:

$^1$H NMR (CDCl3) δ 5.55 (s, 2H), 7.24-7.37 (m, 6H), 7.62 (m, 2H).

HPLC (ISO80-10M) t=5.90 min (96%).

MS: z/e=210 (M+) EI+.

Alternative Synthesis (Preparation 2):

Slowly add a slurry of thioxanthen-9-one (20.0 g, 94.2 mmol) in THF (500 mL) to a chilled (0° C.) solution of methyllithium (1.6M/$Et_2O$, 177 mL, 283 mmol) in THF (100 mL) under $N_2$, keeping temperature below 5° C. Stir translucent brown solution for 1 h at 0° C., then slowly add HCl (4.00M/dioxane, 150 mL, 600 mmol; exothermic reaction with vigorous gas evolution) resulting in an opaque tan slurry. Upon warming to room temperature, add water (200 mL) and extract into ethyl acetate (three 200 mL portions). Dry ($MgSO_4$), filter, and concentrate organics to afford 22.79 g of black oil. HPLC shows 97% purity. Use the product without further purification.

Preparation 3

9-Ethylene-thioxanthine

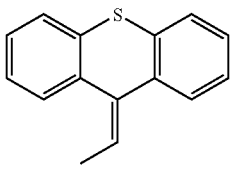

Prepare a suspension of 14.7 g (70 mmol) thioxanthone in 150 mL of THF. Add fifty mL of 3M ethylmagnesium bromide in ether. Heat the reaction mixture to reflux for sixteen hours. Quench the reaction by the addition of 25 mL of 5N HCl and 100 mL of water. Separate and wash the THF layer with a solution of saturated aqueous sodium bicarbonate. Dry the organic layer with anhydrous $Na_2SO_4$ and evaporate down to a brown oil. Re-dissolve the oil in 100 mL of THF and add 10 mL of concentrated sulfuric acid. Stir the reaction and allow to proceed for several hours. Wash the mixture with water, and neutralize with saturated sodium bicarbonate solution. Dry the organic solution with $Na_2SO_4$ and evaporate to an oil. Chromatograph the crude product on silica gel eluting with a solvent of EtOAc-hexane (1:3 v/v). This procedure yields 3 g of the title compound as a tan amorphous powder with following characteristics.

$^1$H NMR (CDCl3) δ 2.02 (d, 3H), 6.05 (q, 1H), 7.18-7.24 (m, 6H), 7.40-7.43 (m, 2).
MS: z/e=223 (M−1) ES−

Preparation 4

9-Bromomethylene thioxanthine

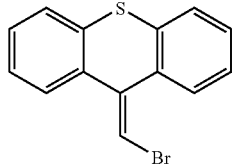

Prepare a solution containing 3.1 g (14.8 mmol) of 9-methylene thioxanthine in 100 mL of methylenechloride. Add to the stirring solution 5.1 g (16 mmol) of pyridine tribromide. Allow the reaction to proceed for seventy-two hours. Terminate the reaction with the addition 200 mL of water. Separate and wash the organic layer with a saturated solution of sodium bicarbonate. Dry the organic solution with $Na_2SO_4$ and evaporate to a dark oil. Chromatograph the crude product on silica gel eluted with a solvent mixture of EtOAc-hexane (1:4 v/v). This yields 1.76 g of the title compound with the following characteristics.

$^1$H NMR (CDCl3) δ 6.67 (s, 1H), 7.24-7.30 (m, 4H), 7.39-7.48 (m, 3H), 7.95 (dd, 1H);
MS: z/e=288,290 (M+)

Preparation 5

9-(1-bromoethylene) thioxanthine

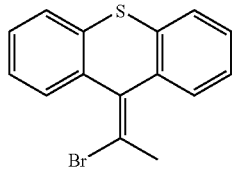

Prepare a solution of 3 g (13.4 mmol) of 9-ethylene thioxanthine in 100 mL of methylenechloride. Stir the solution and add 4.8 g (15 mmol) of pyridine tribromide. Allow the reaction to proceed for sixteen hours and quench with the addition of 100 mL of water. Separate the organic layer and wash with saturated sodium bicarbonate, dry with $Na_2SO_4$, and evaporate to an oil. Chromatograph the crude product on silica gel eluted with EtOAc-hexane (1:4 v/v). This yields 870 mg of the title compound as a dark green oil with the following characteristics.

$^1$H NMR (CDCl3) δ 2.60 (s, 3H), 7.18-7.28 (m, 4H), 7.37 (d, 1H), 7.45 (dd, 2H), 7.77 (d, 1H);
MS: z/e=302, 304 (M+).

EXAMPLE 1

9-[(3-aminophenyl)methylene] thioxanthine

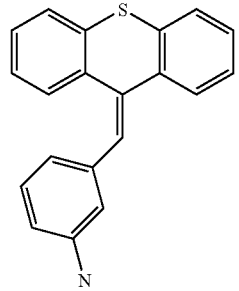

Prepare a solution containing 2.2 g (7.6 mmol) of 9-bromomethylene thioxanthine in 30 mL of 1,4-dioxane and 10 mL of water. Stir the solution and add 2.8 g (15 mmol) of 3-aminophenylboronic acid hemisulfate, followed by the addition of 17 mL (35 mmol) of 2M $Na_2CO_3$ solution and a catalytic amount tetrakis(triphenylphosine)Pd(0). Heat the reaction to reflux. After six hours, add 100 mL of water and extract the entire reaction mixture with several volumes of EtOAc. Wash the organic extract with a brine solution, dry with $Na_2SO_4$, and evaporate to dryness. Purify the crude product by chromatography on silica gel eluted with a mixture of EtOAc-hexane (1:2 v/v). This results in obtaining 740 mg of the title compound as a tan amorphous powder with the following characteristics.

$^1$H NMR (CDCl3) δ 6.83 (s, 1H), 6.88-7.24 (m, 8H), 7.31 (m, 1H), 7.43 (m, 2H), 7.69 (d, 1H);
MS: z/e=302 (M+1) ES+.

EXAMPLE 2

9-[1-(3-aminophenyl)methylene] thioxanthine

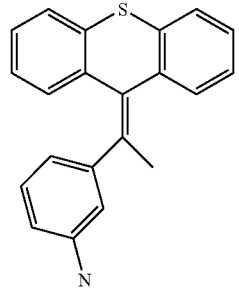

Prepare a solution containing 580 mg (1.9 mmol) of 9-(1-bromoethylene) thioxanthine in 30 mL of 1,4dioxane and 10 mL of water. Stir the solution and add 560 mg (3 mmol) of 3-aminophenylboronic acid hemisulfate, followed by the addition of 3 mL (6 mmol) of 2M $Na_2CO_3$ solution and a catalytic amount tetrakis(triphenylphosine) Pd(0). Heat reaction to reflux. After sixteen hours, check the reaction mixture by TLC and if found not to be complete, add an additional 1.5 g of the boronic acid and 3 mL of the carbonate solution. Reflux for an additional sixteen hours, add 100 mL of water and extract the entire reaction mixture with several volumes of EtOAc. Wash the organic extract with a brine solution, dry with Na$_2$SO$_4$, and evaporate to dryness. Purify the crude product by chromatography on silica gel and elute with a mixture of EtOAc-hexane (1:1 v/v). This results in obtaining 170 mg of the title compound as a white amorphous powder with the following characteristics.

$^1$H NMR (CDCl3) δ 2.26 (s, 3H), 6.36 (s, 1H), 6.46 (br t, 2H), 6.85-7.51 (m, 11H);

MS: z/e=316 (M+1) ES+.

EXAMPLE 3

9-[(3-methylsulfonylaminophenyl)methylene]thioxanthine

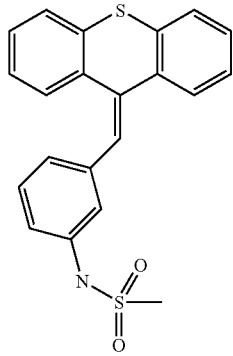

Prepare solution by dissolving 730 mg (2.4 mmol) of 9-[(3-aminophenyl)methylene]thioxanthine in 50 mL of THF. To the solution add 300 mg (3.0 mmol) of triethylamine, a catalytic amount of 4-N,N-dimethylamino pyridine, and 300 mg (2.6 mmol) methylsulfonyl chloride. Stir the reaction mixture at ambient temperature and fit with a drying tube of calcium sulfate. After sixteen hours, evaporate the reaction to dryness and distribute between EtOAc and water. The organic layer is separated and subsequently washed with diluted HCl, diluted NaOH, and water. Dry the EtOAc extract with Na$_2$SO$_4$ and evaporate to dryness. Chromatograph the crude product on silica gel eluted with a solvent of EtOAc-hexane (1:2 v/v). This yields 50 mg of the title compound as a tan amorphous powder with following characteristics.

$^1$H NMR (CDCl3) δ 1.62 (br s, 1H), 2.91 (s, 3H), 6.84 (s, 1H), 6.97-7.49 (m, 11H), 7.70 (d, 1H);

MS: z/e=397 (M+18) ES+378 (M−1) ES−.

EXAMPLE 4

9-[1-(3-methylsulfonoylaminophenyl)ethylene]thioxanthine

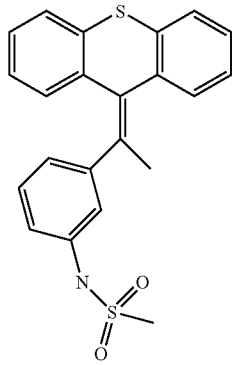

Prepare solution by dissolving 150 mg (0.48 mmol) of 9-[1-(3-aminophenyl)ethylene]thioxanthine in 25 mL of THF. To the solution add 100 mg (1.0 mmol) of triethylamine, a catalytic amount of 4-N,N-dimethylamino pyridine, and 70 mg (0.6 mmol) methylsulfonyl chloride. Stir reaction mixture at ambient temperature and fit with a drying tube of calcium sulfate. After sixteen hours, evaporate reaction to dryness and distribute between EtOAc and water. Separate the organic layer and subsequently wash with diluted HCl, diluted NaOH, and water. Dry the EtOAc extract with Na$_2$SO$_4$ and evaporate to dryness. Chromatograph the crude product on silica gel eluted with a solvent of EtOAc-hexane (1:4 v/v). This yields 50 mg of the title compound as a tan amorphous powder with following characteristics.

$^1$H NMR (CDCl3) δ 2.29 (s, 3H), 2.73 (s, 3H), 6.10 (br s, 1H), 6.69-7.54 (m, 12H);

MS: z/e=411 (M+18)ES+394(M+1) ES+392 (M−1) ES−.

Preparation 6

4-Fluoro-2-(3-fluoro-phenylsulfanyl)-benzonitrile

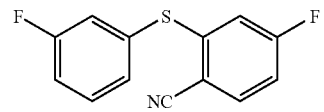

Mix 3-fluorophenol (15.0 g, 117 mmol), 2,4-difluorobenzonitrile (24.4 g, 176 mmol), and K$_2$CO$_3$ (32.3 g, 234 mmol) in THF (150 mL). Stir at room temperature overnight, then dilute with water (150 mL). Extract into ethyl acetate (three 170 mL portions), dry (MgSO$_4$), filter, and concentrate to 35.9 g yellow oil. Purify 15.5 g crude product on 330 g silica gel (0-10% ethyl acetate/hexanes) to obtain 7.88 g of the title product as a colorless oil. Repeat this purification on 15.5 g crude product to obtain 8.08 g of colorless oil. Combine pure lots (15.96 g, 55% yield). MS [EI] 257; HPLC shows 95% purity; $^1$H-NMR consistent with structure. $^1$H-NMR (CDCl$_3$) δ 7.70 (dd, 1H, J=8.8, 5.3 Hz), 7.46 (td, 1H, J=12.5, 3.9 Hz), 7.33 (m, 1H), 7.24 (dt, 1H, J=5.1, 2.8 Hz), 7.18 (m, 1H), 7.02 (m, 1H), 6.82 (dd, 1H, J=9.0, 2.4 Hz).

Preparation 7

3,6-Difluoro-thioxanthen-9-one

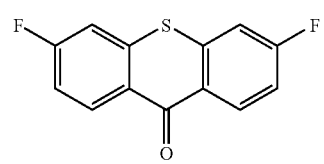

Mix 4-fluoro-2-(3-fluoro-phenylsulfanyl)-benzonitrile (15.7 g, 63 mmol) and polyphosphoric acid (60 g), heat to 200° C. for 10 days. Dilute with H$_2$O (300 mL) and ethyl acetate (700 mL), and filter through a pad of celite. Separate layers formed in the filtrate, and extract aqueous with two 150 mL portions of ethyl acetate. Combine organics, dry (MgSO$_4$), filter, and concentrate to a brown solid. Purify on silica gel (0-10% ethyl acetae/hexanes)to afford 430 mg (3%) of the title compound as a yellow solid. MS [EI] 248; HPLC shows 92% purity; ¹H-NMR consistent with structure. ¹H-NMR (CDCl₃) δ 8.67 (dd, 2H, J=9.0, 5.9 Hz), 7.26 (m, 4H).

Preparation 8

9-Bromomethylene-3,6-difluoro-9H-thioxanthene

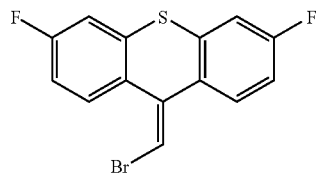

Add portion-wise a slurry of 3,6-difluoro-thioxanthen-9-one (850 mg, 3.42 mmol) in THF (20 mL) to a chilled (0° C.) solution of methyllithium (1.6M/Et₂O, 6.4 mL, 10.3 mmol) in THF (5 mL) under nitrogen. Stir for 90 min at 0° C., then quench reaction with HCl (4.00M/dioxane, 20 mL). Stir at room temperature for 1 h, then dilute with water (50 mL) and extract into ethyl acetate (three 100 mL portions). Dry (MgSO₄), filter, and concentrate organics. Filter through a silica gel plug, eluting with hexanes to give 583 mg of the olefin. Dissolve in CH₂Cl₂ (20 mL) and add DMAP.HBr₃ (1.03 g, 2.84 mmol) Upon stirring at room temperature for 1 h, add 20 mL saturated aqueous Na₂SO₃ and continue stirring for 5 min. Extract into CH₂Cl₂ (three 20 mL portions), dry (MgSO₄) organics, filter, and concentrate. Purify on silica gel (0-10% ethyl acetate/hexanes) to afford 313 mg (28%) of the title compound as a red solid. MS [EI] 324; HPLC shows 79% purity; ¹H-NMR consistent with structure. ¹H-NMR (CDCl₃) δ 7.99 (dd, 1H, J=8.8, 5.7 Hz), 7.45 (dd, 1H, J=8.6, 5.5 Hz), 7.22 (dd, 1H, J=8.6, 2.4 Hz), 7.16 (dd, 1H, J=8.6, 2.4 Hz), 7.06 (m, 2H), 6.68 (s, 1H).

EXAMPLE 5

5-(3,6-Difluoro-thioxanthen-9-ylidenemethyl)-1,3-dihydro-benzoimidazol-2-one

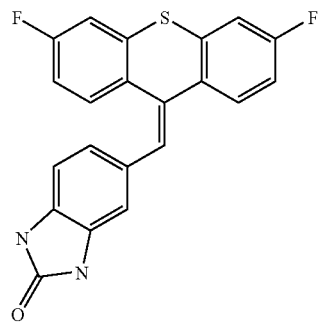

Mix 9-bromomethylene-3,6-difluoro-9H-thioxanthene (104 mg, 0.32 mmol), 5-(4,4,5,5-tetramethyl-[1,3,2]dioxaborolan-2-yl)- 1,3-dihydro-benzoimidazol-2-one (76 mg, 0.29 mmol), and Na₂CO₃ (2M/water, 363 μL, 0.73 mmol) in dioxane (2 mL) and sparge with nitrogen for 5 min. Add Pd(PPh₃)₄ (17 mg, 0.015 mmol), seal vial, and heat to 95° C. overnight. Concentrate and dilute with water (3 mL) and ethyl acetate (10 mL). Load mixture onto a Varian ChemElut CE1005 solid-phase extraction cartridge. Elute, collect, and concentrate 50 mL ethyl acetate. Purify on silica gel (50-60% THF/hexanes), then re-purify by semi-prep reverse-phase HPLC (10-95% CH₃CN/H₂O, 0.1% TFA added) to afford 19 mg (17%) of the title compound as a yellow foam. MS [ES] 379 (M+H), 377 (M−H); HPLC shows 100% purity;, ¹H-NMR (DMSO-d₆) δ 10.67 (s, 1H), 10.54 (s, 1H), 7.89 (dd, 1H, J=8.6, 5.5 Hz), 7.53 (dd, 1H, J=9.0, 2.9 Hz), 7.47 (dd, 1H, J=8.8, 2.6 Hz), 7.27 (m, 2H), 7.02 (m, 2H), 6.86 (dd, 2H, J=11.5, 8.4 Hz), 6.78 (s, 1H).

Table II, below, provides yet additional compounds where Z represents S synthesized according to procedures as described generally in the Schemes above and more particularly as described in Preparations 1-8 and Examples 1-5.

TABLE II

| Example No. | Structure | MS Data | HPLC |
|---|---|---|---|
| 6 | 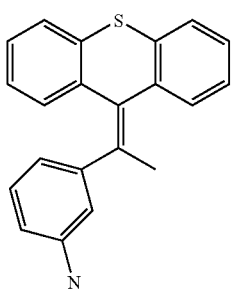 | ES 316 (M + 1) | NA |

TABLE II-continued

| Example No. | Structure | MS Data | HPLC |
| --- | --- | --- | --- |
| 7 | 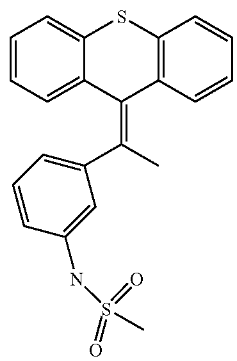 | ES 394 (M + 1) 392 (M − 1) | NA |
| 8 | 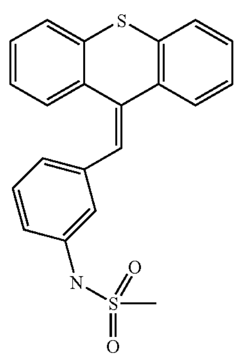 | ES 397 (M + 1 + 18) 378 (M − 1) | NA |
| 9 | 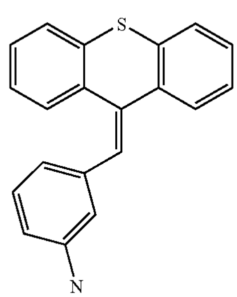 | ES 302 (M + 1) | NA |
| 10 | 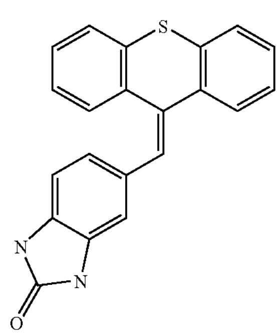 | ES 343 (M + 1) 341 (M − 1) | ISO80-10M) 99% |

TABLE II-continued

| Example No. | Structure | MS Data | HPLC |
|---|---|---|---|
| 11 | 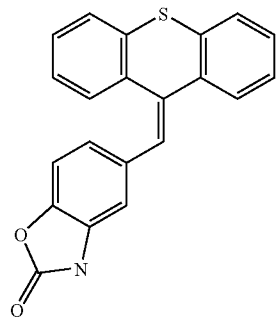 | ES 342 (M − 1) | ISO80-10M) 99% |
| 12 | 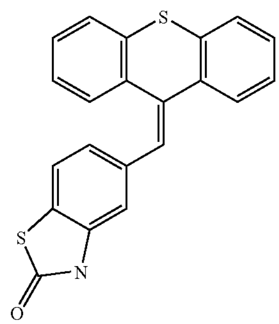 | ES 360 (M + 1) 358 (M − 1) | ISO80-10M) 97% |
| 13 | 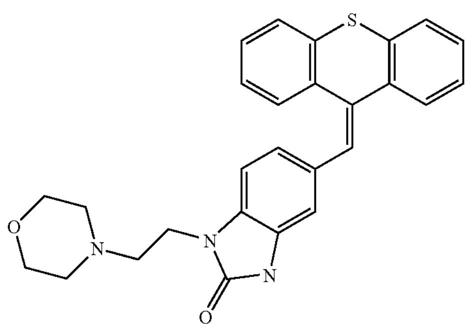 | ES 456 (M + 1) 454 (M − 1) | ISO80-10M) 99% |
| 14 | 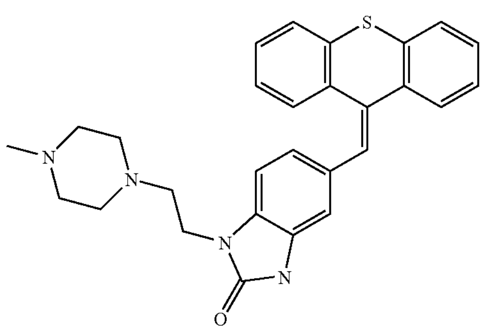 | ES 469 (M + 1) 467 (M − 1) | ISO80-10M) 95% |
| 15 | 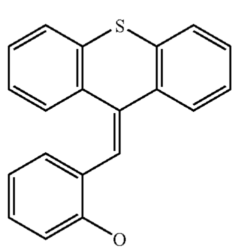 | ES 301 (M − 1) | ISO80-10M) 100% |

TABLE II-continued

| Example No. | Structure | MS Data | HPLC |
|---|---|---|---|
| 16 | 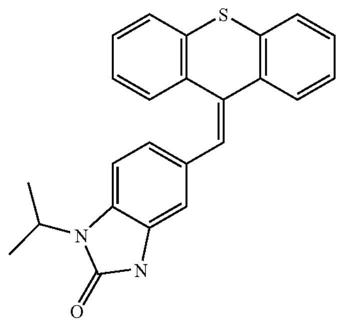 | ES 385 (M + 1) 383 (M − 1) | ISO80-10M) 97% |
| 17 | 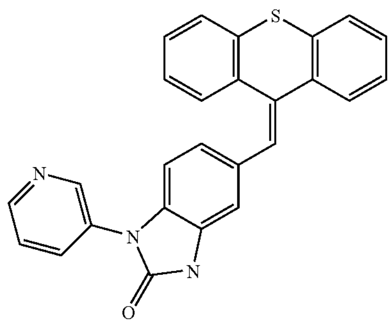 | ES 420 (M + 1) 418 (M − 1) | ISO80-10M) 98% |

Compounds where Z represents CH2

Preparation 9

(9,10-Dihydro-anthracen-9-yl)-(3-methoxy-phenyl)-methanol

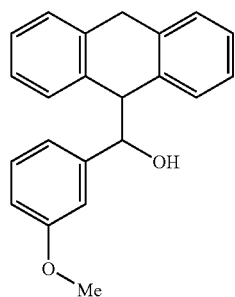

Cool a THF (50 mL) solution of 9,10-dihydroanthracene (5.10 g, 28 mmol) to 0° C. and add 1.6M n-BuLi (19 mL, 30 mmol) slowly. After 30 minutes, add m-anisaldehyde (3.4 mL, 28 mmol) to the dark brown solution. Allow the reaction to slowly warm to ambient temperature and then carefully quench with aqueous saturated NH$_4$Cl. Shake the entire reaction with water/EtOAc and dry the organic layer (MgSO$_4$). Concentrate under reduced pressure to give 9.4 g light tan oil. Purify by column chromatography using 25% EtOAc/hexane to give 4.7 g (53%) as a colorless oil that rapidly crystallized, mp 105.9° C. HPLC shows 94% purity.

EXAMPLE 18

9-(3-Methoxy-benzylidene)-9,10-dihydro-anthracene

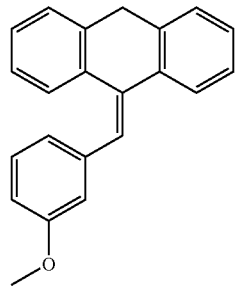

Add 4.1 g (13 mmol) of (9,10-dihydro-anthracen-9-yl)-(3-methoxy-phenyl)-methanol to HOAc (75 mL) containing sulfuric acid (2 mL). Reflux for 2 h and pour into 1.2L ice water. Extract the product into EtOAc and wash with dilute NaOH. Dry (MgSO$_4$) the organic solution, and concentrate to give 4.8 g dark oil. Purify on the ISCO using EtOAc/hexane to give 1.12 g (29%) title compound as a colorless oil. HPLC shows >95% purity. $^1$H NMR (CDCl3) δ3.87 (s, 2H), 3.92 (s, 3H), 6.89-7.47 (m, 13H); MS (CI) 298 (M).

EXAMPLE 19

3-(10H-Anthracen-9-ylidenemethyl)-phenol

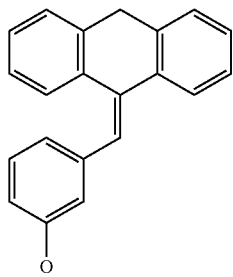

Mix 9-(3-methoxy-benzylidene)-9,10-dihydro-anthracene (900 mg, 3.0 mmol) and pyridine hydrochloride (4 g) and heat at 220° C. for 30 minutes. Cool to 115° C. and carefully add 5N HCl. Extract the product into EtOAc, dry (MgSO$_4$) the organic solution and concentrate to give 720 mg dark oil. Purify by ISCO using EtOAc/hexanes to give title compound, mp 195.8° C., HPLC>99% purify. MS (es) 283 (M−1). $^1$H NMR (DMSO -d6) □3.74 (br s, 1H), 6.79-7.45 (m, 13H), 9.46 (s, 1H); $^{13}$C NMR (DMSO-d6) δ 40.22, 114.59, 115.81, 119.51, 125.53, 125.85, 127.02, 127.30, 128.05, 128.27, 128.56, 129.77, 129.06, 129.39, 134.75, 135.83, 138.98, 139.92, 142.87, 144.63, 157.27

Compounds where Z represents O

Preparation 10

9-Bromomethylene-9H-xanthene

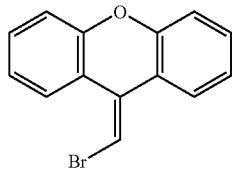

A. Add a suspension of xanthen-9-one (3.00 g, 153 mmol) in THF (50 mL) to a chilled (0° C.) solution of methylmagnesium bromide (3.0M/Et$_2$O, 15.3 mL, 45.9 mmol) in THF (100 mL) under nitrogen. After stirring 30 min at 0° C., slowly add HCl (4.00M/dioxane, 50 mL; exothermic reaction with vigorous gas evolution) and warm up to room temperature. After stirring 30 min, dilute with water (100 mL) and extract into ethyl acetate (three 100 mL portions). Dry (MgSO$_4$), filter, and concentrate organics to a brown oil containing the olefin.

B. Dissolve the olefin from Step A in CH$_2$Cl$_2$ (150 mL), add DMAP.HBr$_3$ and stir at room temperature for 30 min. Dilute reaction with 50 mL saturated aqueous Na$_2$SO$_3$ and extract into CH$_2$Cl$_2$ (three 100 mL portions). Dry (MgSO$_4$), filter, and concentrate organics to an orange oil. Purify on a plug of silica gel eluting with hexanes to afford 2.36 g (56%) of the title compound as a yellow oil. MS [EI] 273; HPLC shows 98% purity; $^1$H-NMR (CDCl$_3$) δ 8.51 (d, 1H, J=8.4 Hz), 7.52 (dd, 1H, J=7.5, 1.3 Hz), 7.44-7.35 (m, 2H), 7.26-7.15 (m, 4H), 6.67 (s, 1H).

EXAMPLE 20

N-(3-Xanthen-9-ylidenemethyl-phenyl)-methanesulfonamide

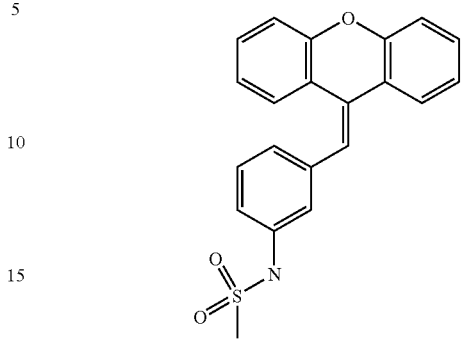

Mix 9-Bromomethylene-9H-xanthene (400 mg, 1.46 mmol), N-[3-(4,4,5,5-Tetramethyl-[1,3,2]dioxaborolan-2-yl)-phenyl]-methanesulfonamide (413 mg, 1.39 mmol), and Na$_2$CO$_3$ (2M/water, 1.74 mL, 3.48 mmol) in dioxane (10 mL) and sparge with nitrogen for 10 min. Add Pd(PPh$_3$)$_4$ (81 mg, 0.070 mmol), seal vial, and heat to 95° C. overnight. Concentrate and dilute with water (3 mL) and ethyl acetate (10 mL). Load mixture onto a Varian ChemElut CE1005 solid-phase extraction cartridge. Elute, collect, and concentrate 50 mL ethyl acetate. Purify on silica gel (20-40% ethyl acetate/hexanes), then re-purify by semi-prep reverse-phase HPLC (10-95% CH$_3$CN/H$_2$O, 0.1% TFA added) to afford 14 mg (3%) of the title compound as a yellow solid. MS [ES] 364 (M+H), 362 (M−H); HPLC shows 97% purity; $^1$H-NMR (CDCl$_3$) δ 7.78 (d, 1H, J=7.5 Hz), 7.39-7.14 (m, 10H), 6.91 (s, 1H), 6.85 (t, 1H, J=7.5 Hz), 6.53 (s, 1H), 3.01 (s, 3H).

We claim:

1. A compound of the formula:

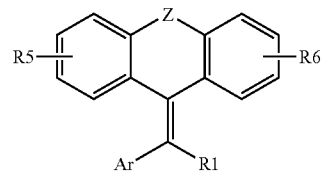

Formula I wherein,

Z represents CH$_2$, S, or O;

Ar represents a group of the formula:

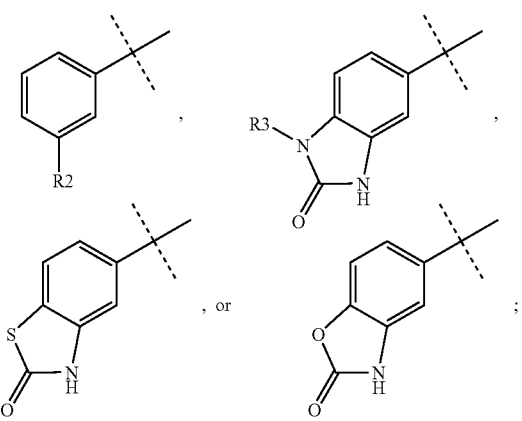

$R^1$ represents hydrogen or $(C_1-C_6)$alkyl;

$R^2$ represents amino or $NH\,SO_2R^4$;

$R^3$ represents hydrogen, $(C_1-C_6)$alkyl, heterocycle, substituted heterocycle, $(C_1-C_4)$alkyl-heterocycle, or $(C_1-C_4)$alkyl-substituted heterocycle, provided that where Ar represents:

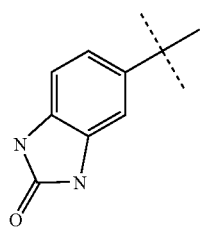

then Z is other than O;

$R^4$ represents independently at each occurrence $(C_1-C_6)$alkyl;

$R^5$ and $R^6$ represent independently at each occurrence hydrogen, fluoro, chloro, hydroxy, difluoromethyl, trifluoromethyl, $(C_1-C_6)$alkoxy, $(C_1-C_4)$alkyl-$(C_3-C_7)$cycloalkyl, $(C_1-C_4)$alkoxy-$(C_3-C_7)$cycloalkyl, $NHR^7$, or $N(R^7)_2$ wherein R7 represents independently at each occurrence $(C_1-C_6)$alkoxy or $(C_3-C_7)$cycloalkyl;

or a pharmaceutically acceptable salt thereof.

2. The compound according to claim 1 wherein R1 represents hydrogen, methyl or ethyl.

3. The compound according to claim 2 wherein R1 represents hydrogen.

4. The compound according to claim 1 wherein Z represents S or O.

5. The compound according to claim 4 wherein Z represents S.

6. The compound according to claim 1 wherein Ar represents a group of the formula:

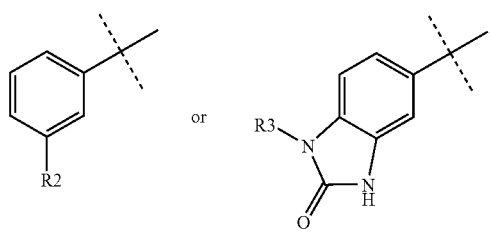

7. The compound according to claim 6 wherein Ar represents a group of the formula:

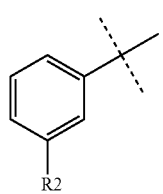

8. The compound according to claim 7 wherein R2 represents $NH\,SO_2CH_3$.

9. The compound according to claim 6 wherein Ar represents a group of the formula:

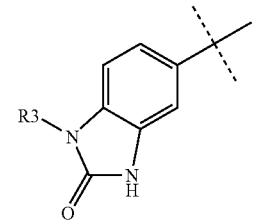

10. The compound according to claim 9 wherein R3 represents hydrogen, methyl, ethyl, isopropyl, heterocycle, substituted heterocycle, $(C_1-C_4)$alkyl-heterocycle, or $(C_1-C_4)$alkyl-substituted heterocycle.

11. The compound according to claim 1 wherein $R^5$ and $R^6$ represent independently at each occurrence hydrogen or flouro.

12. A compound selected from the group consisting of

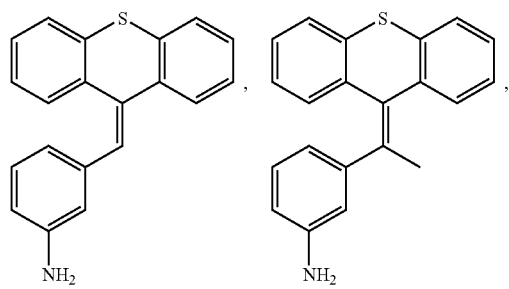

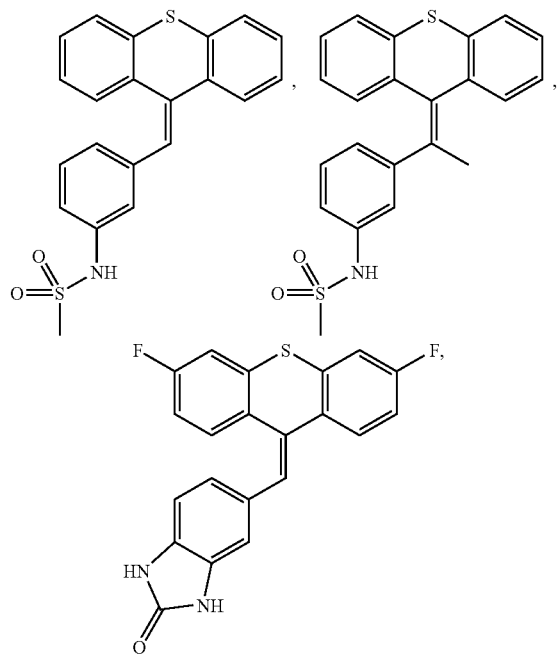

-continued
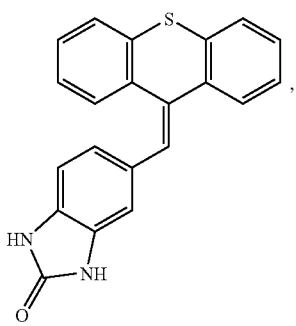
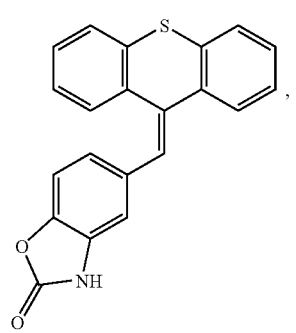
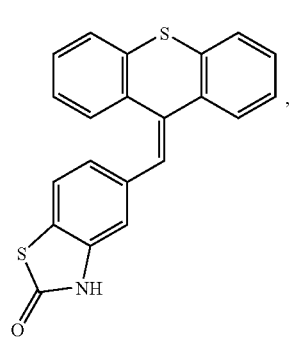
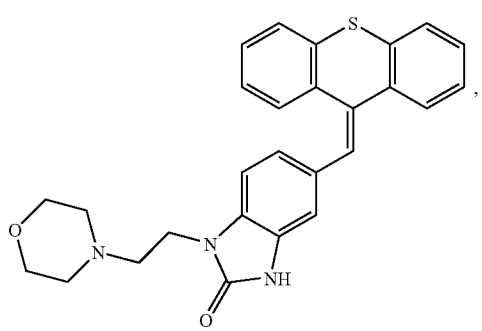
-continued
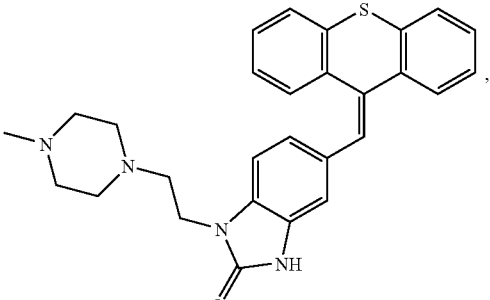
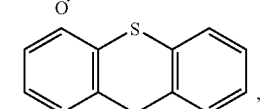
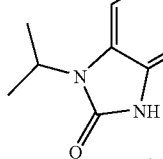
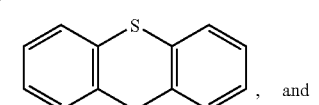
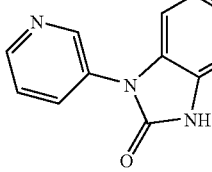
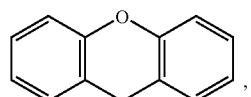
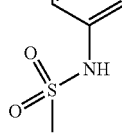
or a pharmaceutically acceptable salt thereof.
13. A pharmaceutical composition comprising the compound according to claim 1 in combination with a pharmaceutically acceptable carrier, diluent, or excipient.
* * * * *